United States Patent [19]

Shimotani et al.

[11] Patent Number: 5,598,145
[45] Date of Patent: Jan. 28, 1997

[54] DRIVER PHOTOGRAPHING APPARATUS

[75] Inventors: Mitsuo Shimotani; Minoru Nishida; Akira Okada; Yoshiharu Morihiro, all of Hyogo, Japan

[73] Assignee: Mitsubishi Denki Kabushiki Kaisha, Tokyo, Japan

[21] Appl. No.: 288,936

[22] Filed: Aug. 10, 1994

[30] Foreign Application Priority Data

Nov. 11, 1993 [JP] Japan ................................. 5-282502

[51] Int. Cl.$^6$ ............................................. G08B 23/00
[52] U.S. Cl. ............................................. 340/576; 180/272
[58] Field of Search .................................. 340/576, 575; 180/272

[56] References Cited

U.S. PATENT DOCUMENTS

| 2,726,380 | 12/1955 | Campisi | 340/575 X |
| 4,397,531 | 8/1983 | Lees | 340/576 X |
| 4,854,329 | 8/1989 | Walruff | 340/576 X |
| 5,402,109 | 3/1995 | Mannik | 340/576 X |

FOREIGN PATENT DOCUMENTS

| 4122752 | 1/1993 | Germany . |
| 158303 | 8/1985 | Japan . |
| 2133598 | 7/1984 | United Kingdom | 340/575 |
| 2215040 | 9/1989 | United Kingdom | 340/575 |

OTHER PUBLICATIONS

Merchant, Morrissette & Porterfield "Remote Measurement of Eye Direction Allowing Subject Motion Over One Cubic Foot of Space" IEEE Transactions on Biomedical Engineering, Jul. 1974, vol. BME–21, No. 4.

Patent Abstracts of Japan, vol. 9, No. 334, p. 103 (Pub. No. 60–158303), Dec. 1985.

Primary Examiner—Thomas Mullen
Attorney, Agent, or Firm—Wolf, Greenfield & Sacks, P.C.

[57] ABSTRACT

A driver photographing apparatus that photographs images from reflections on the retinas of a driver in a vehicle having disturbance light using signal processing techniques. The apparatus comprises a light source for illuminating the driver with a first light beam along a first optical path, and a sensor that inputs a second light beam, along a second optical path, that includes reflections from the driver and disturbance light, to form an image of the driver. The light source and the sensor are disposed such that the first and second optical paths are along substantially the same axis. The apparatus further includes a processing circuit that eliminates the effect of the disturbance light on the image of the driver, and a detecting circuit that determines the action of the driver based on the driver's image.

13 Claims, 29 Drawing Sheets

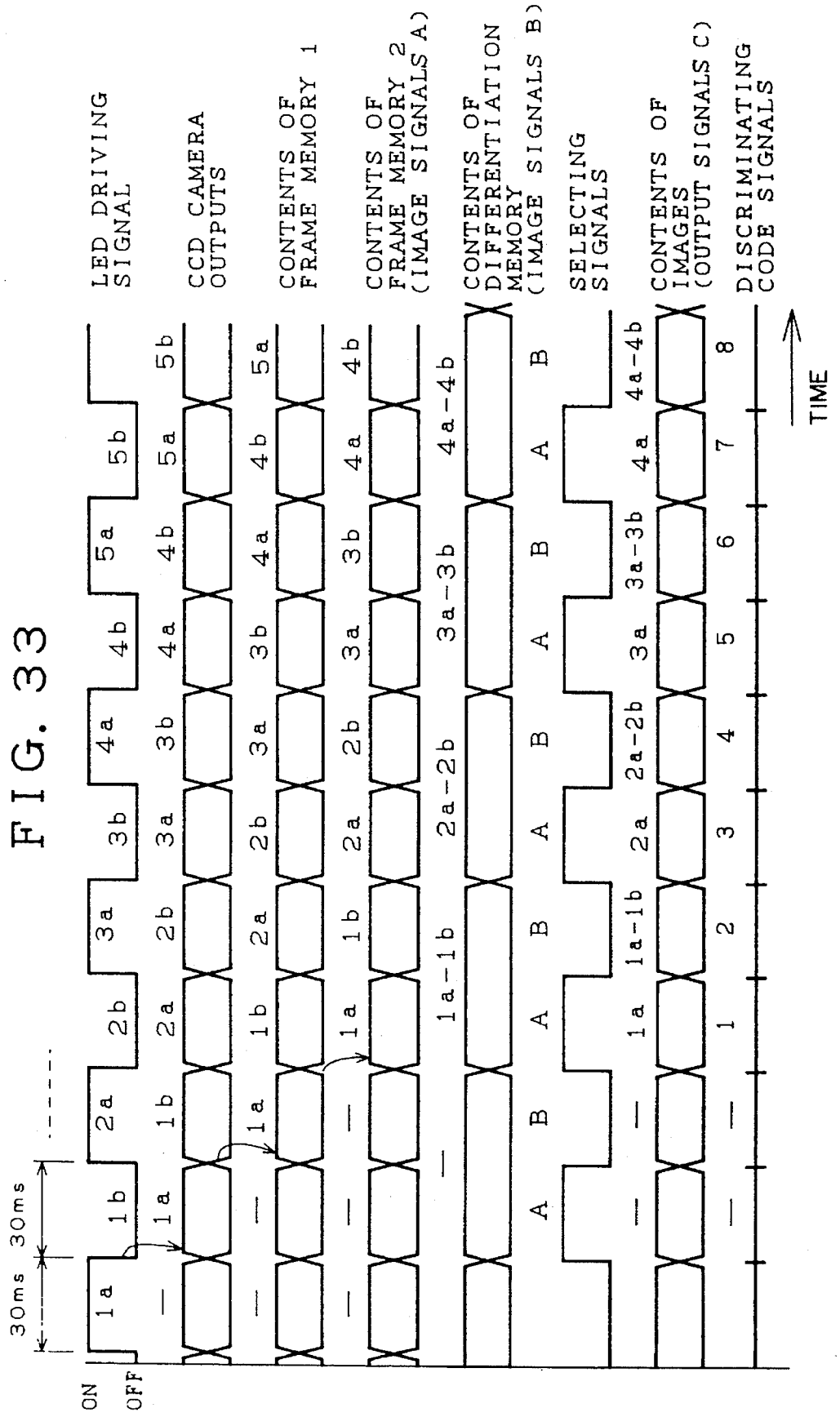

DRIVER PHOTOGRAPHING APPARATUS

BACKGROUND OF THE INVENTION

1. Field of the Invention

This invention relates to a driver photographing apparatus for detecting driver's actions such as dozing, looking aside and the like.

2. Description of the Prior Art

FIG. 1 is a block diagram of an eye position detector using a prior art driver photographing apparatus shown in, for example, Japanese Published Unexamined Patent Application No. 158303 of 1985. In FIG. 1, reference numeral 1 designates a driver; numeral 2 designates a driver's seat; numeral 3 designates an instrument panel; numerals 10a, 10b designate CCD cameras; numeral 20 designates an infrared ray LED; numeral 21 designates an LED driving circuit supplying electric current to the infrared ray LED 20; and numeral 100 designates a driver's action detecting circuit.

Next, the operation of the prior art will be described.

The infrared ray LED 20 irradiates the driver 1 in the driver's seat 2. The images of the driver 1 are input to the CCD cameras 10a, 10b placed at the positions where the cameras 10a, 10b can photograph a prescribed region including the face of the driver 1. The input images to the CCD cameras 10a, 10b are further input to the driver's action detecting circuit 100 from the cameras 10a, 10b as image signals, then the data of eye positions, the directions of the face and the like are processed by means of image processing techniques. FIG. 2 is a sample of an infrared image obtained in such a way. In FIG. 2, reference numeral 4 designates an iris; numeral 5 designates a sclera; numeral 6 designates a pupil; and numeral 7 designates a face surface. In the image obtained in such a way, the sclera 5 is displayed a little darker in comparison with the face surface 7, and the iris 4 is displayed a little darker in comparison with the sclera 5, and further the pupil 6 is displayed still darker.

Because the prior art driver photographing apparatus is composed as described above, it has a problem that complicated image processing techniques are necessary to detect the positions of pupils 6. That is to say, the apparatus searches the pupils 6, for example, as follows: executing filtering operations, detecting edges, and pattern recognizing by executing the Hough transformation processing and the like for obtaining circles corresponding to the pupils 6 from the detected edge shapes. Moreover, the prior art apparatus has another problem that if the edges are not detected finely because of noises and the like at the time of the edge detection, the circles are not obtained and the image processings become very complicated, and time-consuming.

On the other hand, as shown in the article titled "THE EXTRACTION OF PUPILS AND A TRIAL PRODUCTION OF A SIGHT LINE DETECTING APPARATUS WHICH PERMITS THE MOVEMENTS OF HEAD PARTS" (DENSHI JOHO TUSHIN GAKKAI RONBUNSHI (TILE PAPERS JOURNAL OF THE ELECTRIC AND INFORMATION COMMUNICATION SOCIETY OF JAPAN), D-II, Vol. J76-D-II, No. 3), if a face is irradiated by a coaxially irradiating apparatus, images reflected on retinas can be clearly photographed, then positions of the pupil can be detected by very simple image processings such as, for example, transformation to a binary image from a grey image. (The "coaxially irradiating illuminating" means illuminating in a configuration where the optical axis of a camera and the irradiating direction of the illuminating light coincide with each other). It is accordingly thinkable to use this apparatus as a driver photographing apparatus, but the actual realization of it brings about a problem that the images reflected on retinas can not be obtained because there is disturbance light (or sunlight) whose light intensity is not less than 100 times through 1,000 times that of the illuminating light for photographing under the condition of being installed in cars. FIG. 3(a) and FIG. 3(b) are explanatory drawings for explaining influence caused by the aforementioned disturbance light. The waveshapes shown in FIG. 3(b) show the brightness distributions along the line A—A of an obtained face image (FIG. 3(a)). The curved line A of FIG. 3(b) designates the brightness distribution of a daytime image in fine weather which is photographed in the coaxially irradiating method; the curved line B designates the brightness distribution of another daytime image in rainy weather which is photographed in the same coaxially irradiating method; the curved line C designates the brightness distribution of a nighttime image which is photographed in the same coaxially irradiating method; and the curved line D designates the brightness distribution of another nighttime image which is photographed in an uncoaxially irradiating method (i.e. prior art construction). It can be found that the brightness of the parts of the images, other than the pupils 6, photographed in the coaxially irradiating method becomes higher in accordance with disturbance light's enlargement (the curved line C: in the nighttime → the curved line B: in the daytime in rainy weather →the curved line A: in the daytime in fine weather), and that the identification of the pupils 6 becomes correspondingly more difficult.

SUMMARY OF THE INVENTION

In view of the foregoing, it is an object of the present invention to provide a driver photographing apparatus which can detect pupil positions by means of simple image processing techniques and which can photograph images reflected on the retinas of a driver simply and clearly even if the apparatus is installed in a car.

It is another object of the invention to provide a driver photographing apparatus which can obtain clear images reflected on retinas even if disturbance light is strong.

It is a further object of the invention to provide a driver photographing apparatus which can eliminate the images formed by disturbance light by decreasing the influence of temperature changes.

It is a further object of the invention to provide a driver photographing apparatus which can photograph obvious images reflected on retinas.

It is a further object of the invention to provide a driver photographing apparatus which can photograph obvious images reflected on retinas by eliminating the influence of disturbance light by means of signal processing techniques.

It is a further object of the invention to provide a driver photographing apparatus which can photograph obvious images reflected on retinas even when eyes move rapidly.

It is a further object of the invention to provide a driver photographing apparatus which can photograph obvious images reflected on retinas even hen eyes move still more rapidly.

It is a further object of the invention to provide a driver photographing apparatus which can photograph obvious images reflected on retinas by eliminating the influence of disturbance light by means of providing an image processing means.

It is a further object of the invention to provide a driver photographing apparatus which can always obtain distinct images reflected on retinas by making the contrasts of obtained face images constant.

It is a further object of the invention to provide a driver photographing apparatus which can photograph obvious images reflected on retinas and which can catch other features of a driver even in the nighttime.

It is a further object of the invention to provide a driver photographing apparatus which can always obtain distinct images reflected on retinas by making the contrasts of obtained face images constant by means of irradiating a driver at a constant illuminance always.

According to the first aspect of the present invention, for achieving the above-mentioned objects, there is provided a driver photographing apparatus disposing an illuminating means and a light input means, to which the light forming driver images is input, in such a way that the irradiating direction of illuminating light and the light axis connecting the light input means with the driver takes almost the same axis at least near the driver.

As stated above, the driver photographing apparatus according to the first aspect of the invention is constructed to utilize the coaxial irradiating, and consequently pupil positions can be detected with simple image processing techniques.

According to the second aspect of the invention, there is provided a driver photographing apparatus disposing a disturbance light limiting means, which passes light components of an illuminating means and limits the disturbance light input into the interior of a car, on the optical path connecting a light input means with a driver.

As stated above, the driver photographing apparatus according to the second aspect of the invention is provided with a filter, which limits the disturbance light, disposed on the optical path connecting the light input means with the driver, and consequently, distinct images reflected on retinas can be obtained even if the disturbance light is strong.

According to the third aspect of the invention, there is provided a driver photographing apparatus disposing a disturbance lighting limiting means which passes light components of an illuminating means and limits the disturbance light input into the interior of a car, on the optical path connecting a light illuminating means with a driver and further connecting a light input means with the driver.

As stated above, the driver photographing apparatus according to the third aspect of the invention is provided with a filter disposed on the optical path connecting the light illuminating means with the driver and further connecting the light input means with the driver. Consequently, the influence of temperature change can be decreased and the disturbance light can be limited.

According to the fourth aspect of the invention, there is provided a driver photographing apparatus provided with a wavelength characteristic compensating means compensating the influence of shifting of the central wavelength of an illuminating means according to the change of the central wavelength of the illuminating means.

According to the fifth aspect of the invention, there is provided a driver photographing apparatus provided with plural disturbance light limiting means having different transmission characteristics from each other, and the apparatus constructed in such a way that a wavelength characteristic compensating means exchanges the aforementioned disturbance light limiting means according to the central wavelength changes of an illuminating means.

According to the sixth aspect of the invention, there is provided a driver photographing apparatus provided with an illuminating means composed of plural monochromatic light emitting devices having different wavelength characteristics from each other, and the apparatus constructed in such a way that a wavelength characteristics compensating means exchanges the aforementioned monochromatic light emitting devices having emission wavelength resembled to pass wavelengths of a disturbance light limiting means according to the central wavelength changes of the aforementioned monochromatic light emitting device.

As stated above, in the driver photographing apparatus according to the fourth to the sixth aspects of the invention, even if emitted light wavelengths' shiftings of LEDs would be caused by temperature change and the like, the wavelength characteristics compensating means compensates the influence of the shiftings, and consequently, the apparatus can photograph obvious images reflected on retinas.

According to the seventh aspect of the invention, there is provided a driver photographing apparatus comprising an illuminating light controlling means controlling the existence of illuminating light, and an image processing means outputting the driver image signals when the illuminating light exists and the driver image signals when the illuminating light does not exist, or image signals generated by operating the difference of both of the aforementioned image signals.

As stated above, the driver photographing apparatus according to the seventh aspect of the invention obtains the image signals of the driver both in the case where the illuminating light exists or not, and the apparatus obtains images reflected on retinas from the difference image signals of both of the aforementioned image signals. Consequently, the influence of disturbance light is eliminated by the signal processings, and the obvious images reflected on the retinas can be photographed.

According to the eighth aspect of the invention, there is provided a driver photographing apparatus whose light input means has a light input controlling means inputting driver's images to the apparatus for a prescribed time period corresponding to the existence of illuminating light.

As stated above, the driver photographing apparatus according to the eighth aspect of the invention is constructed to input the images of the driver to the apparatus for the prescribed time period corresponding to the existence of the illustrating light, and consequently, the time intervals taking in each image corresponding to the existence of the illuminating light can be shortened, and blurrings become smaller. Thus, obvious images can be photographed even if the movement of the driver is fast.

According to the ninth aspect of the invention, there is provided a driver photographing apparatus in which a light input controlling means continuously inputs images of a driver for a prescribed time period spreading over both of the time periods when illuminating light exists and does not exist respectively.

As stated above, in the driver photographing apparatus according to the ninth aspect of the invention, the time difference between the time period taking in the images when the illuminating light exists and the time period taking in the images when the illuminating light does not exist can be decreased to be very small, and consequently, the differences of the existence of the illuminating light appear on the obtained difference images. Thus, obvious images can be photographed even if the movement of the driver is rapid.

According to the tenth aspect of the invention, there is provided a driver photographing apparatus provided with disturbance light limiting means having different wavelength characteristics from each other and two light input means to which the light from each disturbance light limiting means is input, and further the apparatus comprising an image processing means outputting each image signal obtained by each light input means or the image signal generated by operating the difference of each of the aforementioned image signals.

As stated above, the driver photographing apparatus according to the tenth aspect of the invention is provided with the light input means to which, the light from each disturbance light limiting means is input, and the apparatus obtains the images of a driver photographed with illuminating light and the images of the driver photographed without the illuminating light, and further the apparatus obtains images reflected on retinas from the difference images of both of the aforementioned images. Consequently, the influence of the disturbance light is removed by the signal processings, and obvious images reflected on retinas can be photographed.

According to the eleventh aspect of the invention, there is provided a driver photographing apparatus constructed to change illuminating light intensity according to the illuminance in the interior of a car.

According to the twelfth aspect of the invention, there is provided a driver photographing apparatus having a first illuminating means disposed in such a way that an illuminating light irradiating direction and the optical axis of a light input means take almost the same axis near a driver, and a second illuminating means illuminating the driver, the second illuminating means being disposed at a different position from that of the first illuminating means, and further the second illuminating means being constructed to change the illuminating light intensity according to the illuminance in the interior of a car.

As stated above, the driver photographing apparatus according to the eleventh and the twelfth aspects of the invention are constructed to change the illuminating light intensity of an irradiating means or the illuminating light intensity of the second illuminating means disposed on the different position from that of the first illuminating means, and consequently, the contrast of obtained face images becomes constant, and distinct images reflected on retinas always can be obtained.

According to the thirteenth aspect of the invention, there is provided a driver photographing apparatus comprising a first illuminating means disposed in such a way that an illuminating light irradiating direction and the light axis of a light input means take almost the same axis near a driver, a second illuminating means disposed on a different position from the first illuminating means and illuminating the driver, and an exchanging means exchanging the first illuminating means and the second illuminating means to illuminate the driver.

As stated above, the driver photographing apparatus of the invention according to the thirteenth aspect of the invention exchanges the first illuminating means and the second illuminating means to illuminate the driver, and the apparatus operates the difference images of each obtained image in conformity with the exchanging of each illuminating means, and consequently, obvious images reflected on retinas can be photographed. Furthermore, because the images obtained by the second illuminating means have much information, other features of the driver can be obtained even in the nighttime by exchanging illumination to the second illuminating means by means of the exchanging means.

According to the fourteenth aspect of the invention, there is provided a driver photographing apparatus having a range finding means measuring the distance between a driver and an illuminating means, and the apparatus changing illuminating light intensity in conformity with the distance.

As stated above, the driver photographing apparatus according to the fourteenth aspect of the invention can change the illuminating light intensity in conformity with the distance between the driver and the illuminating means, and consequently, the driver can be illuminated at a constant illuminance always, and the contrast of obtained images becomes constant. Thus distinct images reflected on retinas always can be obtained.

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

BRIEF DESCRIPTION OF THE DRAWINGS

FIG. 33 is a timing chart for explaining the operation of the driver photographing apparatus of the embodiment 21 of the invention.

DETAILED DESCRIPTION OF THE PREFERRED EMBODIMENTS

Preferred embodiments of the invention will now be described in detail on reference to the accompanying drawings.

EMBODIMENT 1.

Figure 1:
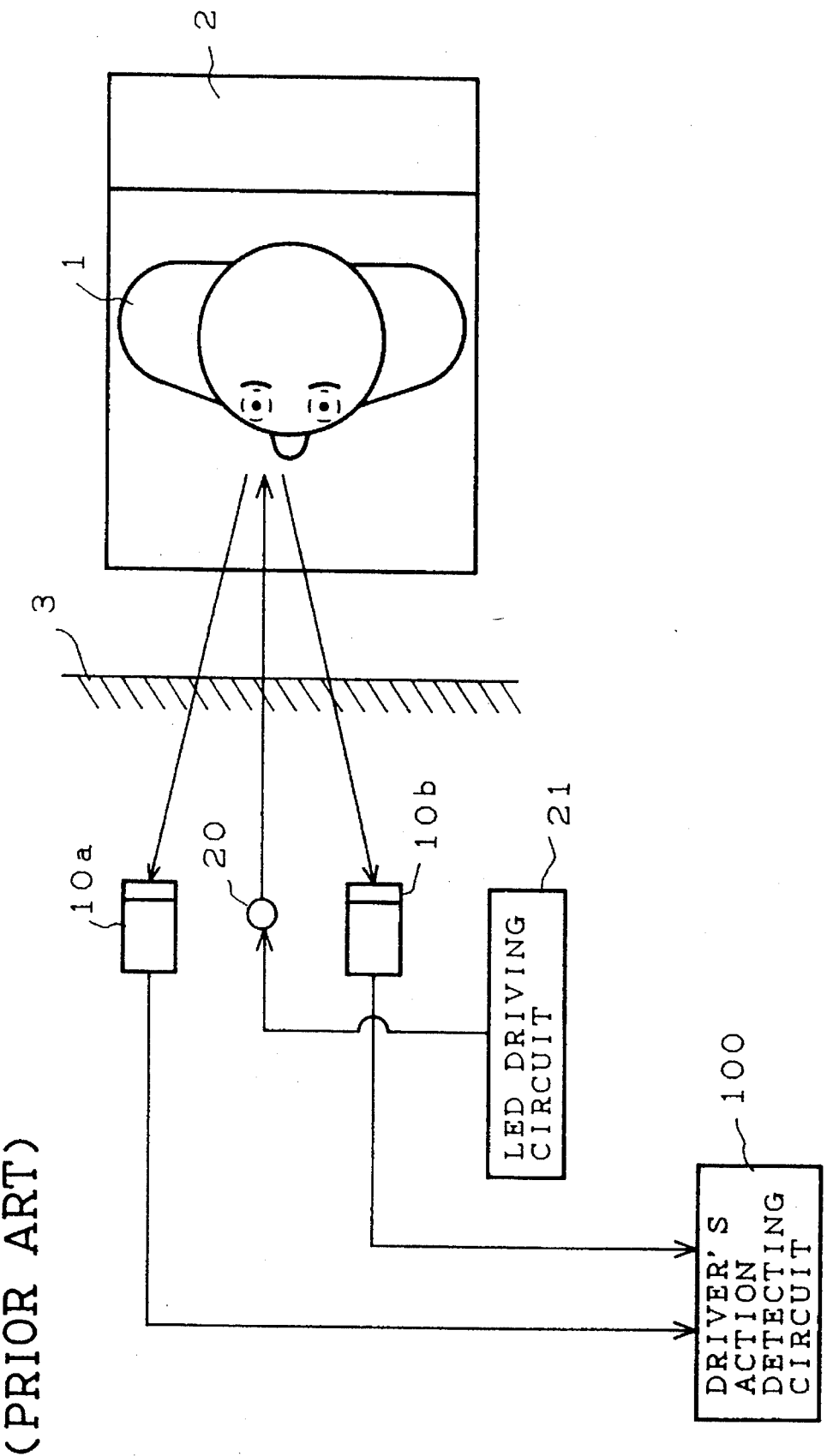
FIG. 1 is a block diagram showing a prior art driver photographing apparatus.
Figure 2:
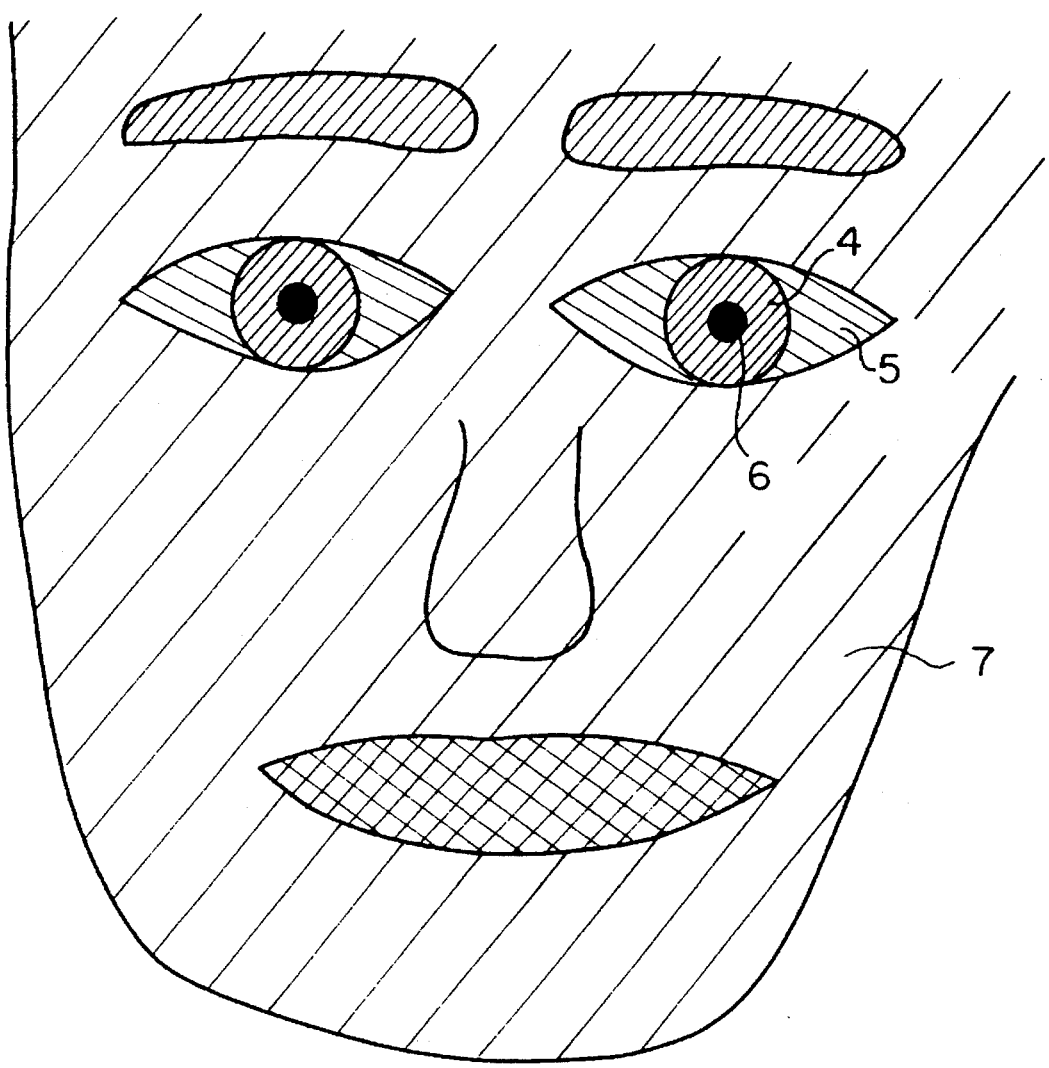
FIG. 2 is an explanatory drawing showing a photographed image of a driver photographed by the prior art driver photographing apparatus.
Figure 3A:
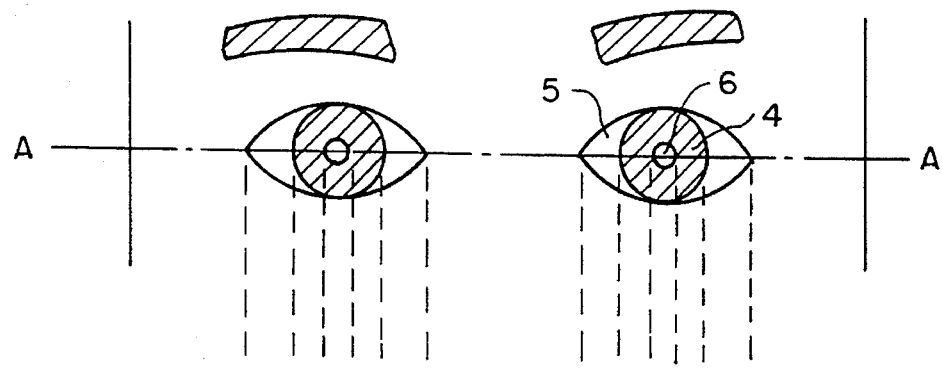
FIG. 3(a) and FIG. 3(b) are explanatory drawings for explaining the influence of disturbance light in a driver photographing apparatus.
Figure 3B:
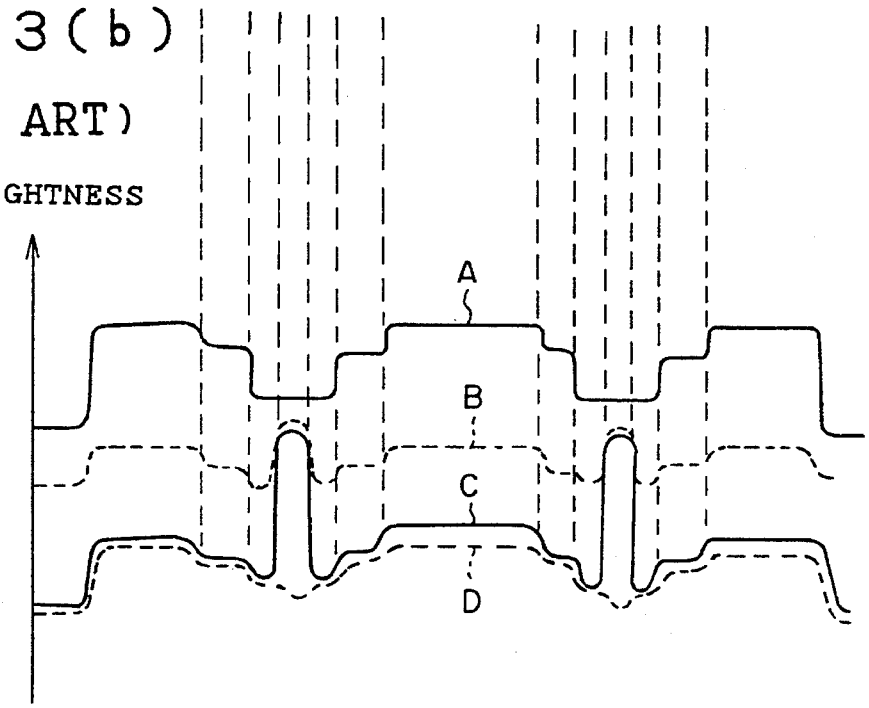
Figure 4:
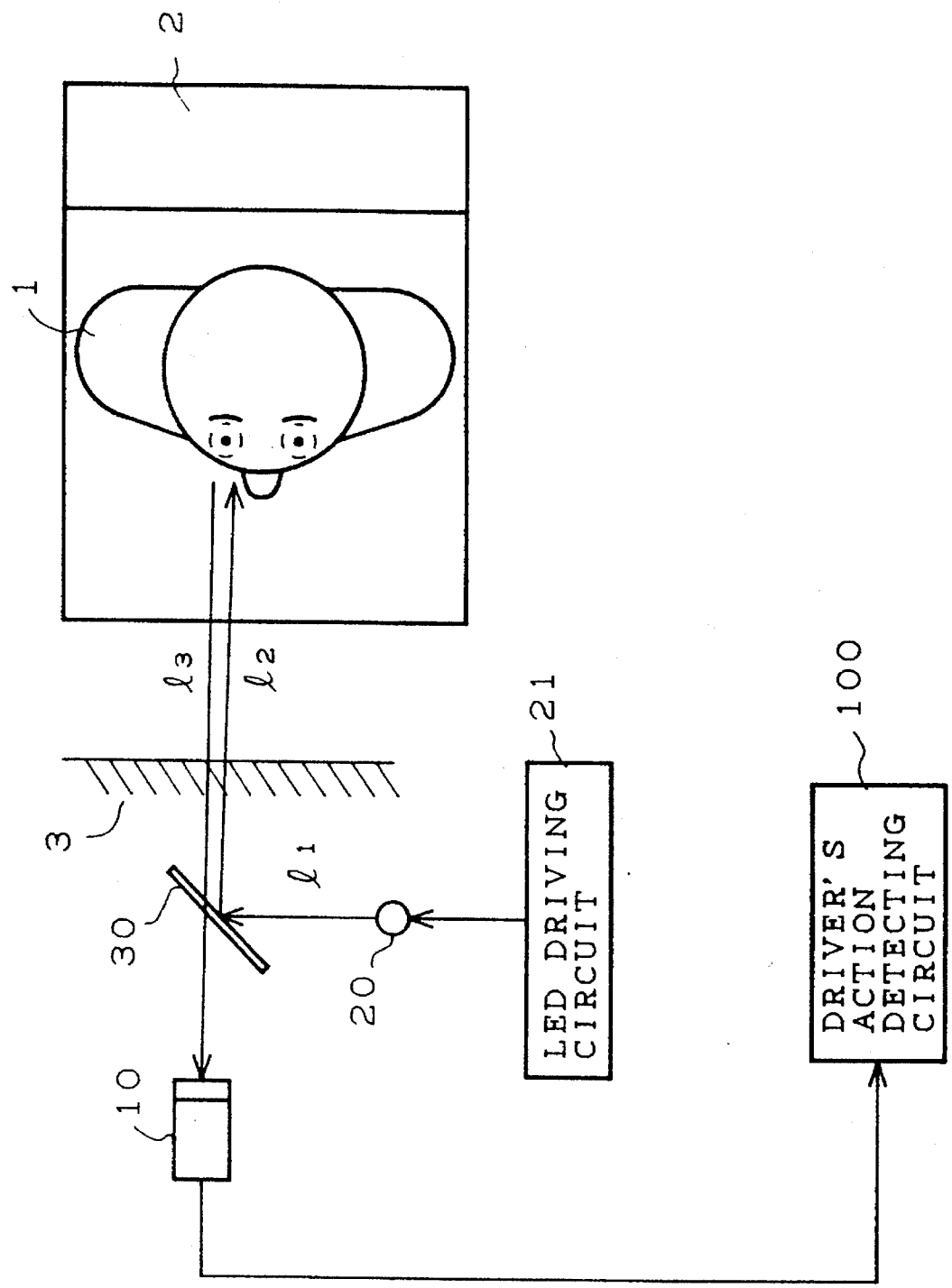
FIG. 4 is a block diagram showing the driver photographing apparatus of the embodiment 1 of the present invention.

FIG. 4 is a block diagram showing the driver photographing apparatus of the embodiment 1 of the present invention. In FIG. 4, reference numeral 10 designates a CCD camera (light input means) disposed at a position capable of photographing a prescribed region including the face of the driver 1; numeral 20 designates an illuminating means illuminating the driver 1 in the driver's seat 2, the illuminating means 20 being, for example, an infrared ray LED whose emitted light central wavelength is 860 nm and whose light emitting directional characteristic is ±20; and numeral 30 designates a half mirror. Moreover, the apparatus constructed like in FIG. 4 is suitable for photographing in the nighttime.

Next, the operation of this apparatus will be described.

Figure 5:
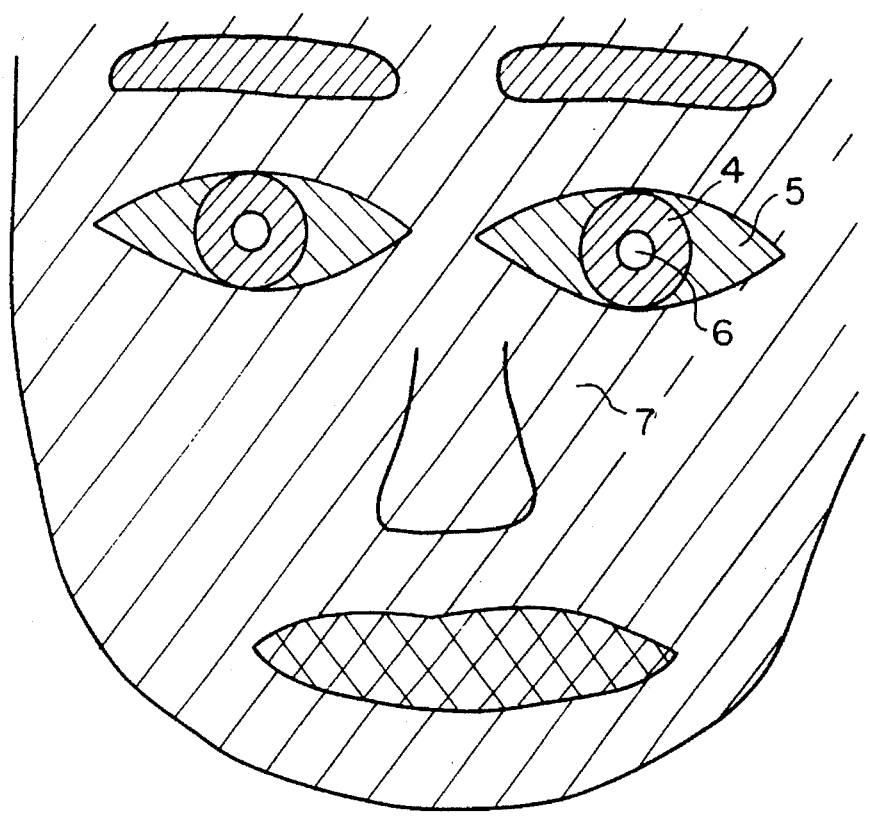
FIG. 5 is an explanatory drawing showing a photographed image of a driver photographed by the driver photographing apparatus of the embodiment 1 of the invention.
Figure 6:
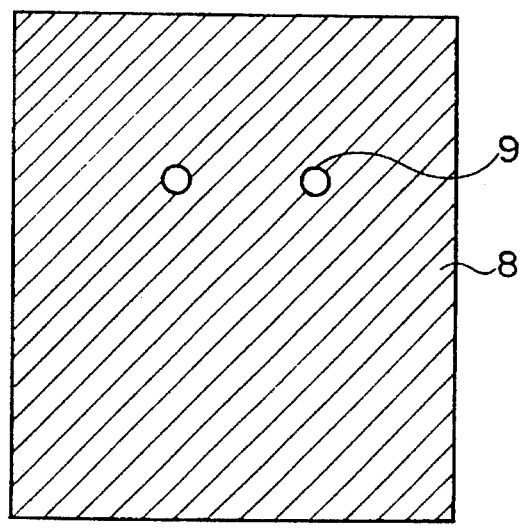
FIG. 6 is an explanatory drawing showing a photographed image processed by the driver photographing apparatus of the embodiment 1 of the invention.

In FIG. 4, half the mirror 30 reflects the half amount of the illuminating light irradiated along the optical path 11, and the reflected light illuminates the face of the driver 1 along the optical path 12. The image of the driver 1 reaches the half mirror 30 along the optical path 13, and the half amount of the light reaches the CCD camera 10. Such that the CCD camera 10 takes the image of the driver 1 in. In this case, the axes of the optical path 12 and 13 are arranged to be almost coaxial or within a prescribed angle (for example, 2°) from the view point of the driver 1 (the coaxial irradiating illumination). In this embodiment, the angle is set to be 0°, and the angle of the half mirror 30 to the light axis 13 of the CCD camera 10 is 45°. In this case, the photographed image of the driver 1 is obtained as it is shown in FIG. 5. In FIG. 5, the pupils 6 are observed as if they are shining owing to the light reflected on the retinas by the coaxial irradiating illumination of the aforementioned arrangement, and the pupils 6 are photographed in a very high brightness state in comparison with other features such as the face surface 7 and the like. This is the reason why pupils 6 have properties that they return reflected light in the same direction as that of the incident light. Consequently, binary images such as images 8 and 9, shown in FIG. 6 can be obtained from the grey images by adjusting a threshold value of the transformation to a binary image from a grey image. The image shown in FIG. 6 is constituted of only two circular white regions 9 corresponding to the pupils 6 and the other black region 8. Thus, the positions of the pupils 6 can be detected easily by simple operations such as an operation deducing a gravity center and the like without complex operation processings.

Moreover, though the aforementioned embodiment 1 uses the infrared ray LED as the illuminating means 20, an illuminating means composed of a halogen lamp emitting wide wavelength band width light or an illuminating means composed of a halogen lamp and a filter passing specific wavelength light into its spectral components may be used.

EMBODIMENT 2.

In the nighttime, the images reflected on retinas appear obviously in the embodiment 1, accordingly high brightness regions can be detected as pupils. However, in the daytime, because disturbance light such as sunlight finds its way into the interior of a car, the brightness of the parts of eyes other than the pupils, illuminated by the disturbance light, becomes very high. Consequently, the photographing by means of the coaxial irradiating illumination becomes not capable of obtaining obvious images reflected on retinas. The embodiment 2 of the invention is an example devised to decrease the influence of the disturbance light and to be able to photograph the images reflected on retinas obviously.

Figure 7:
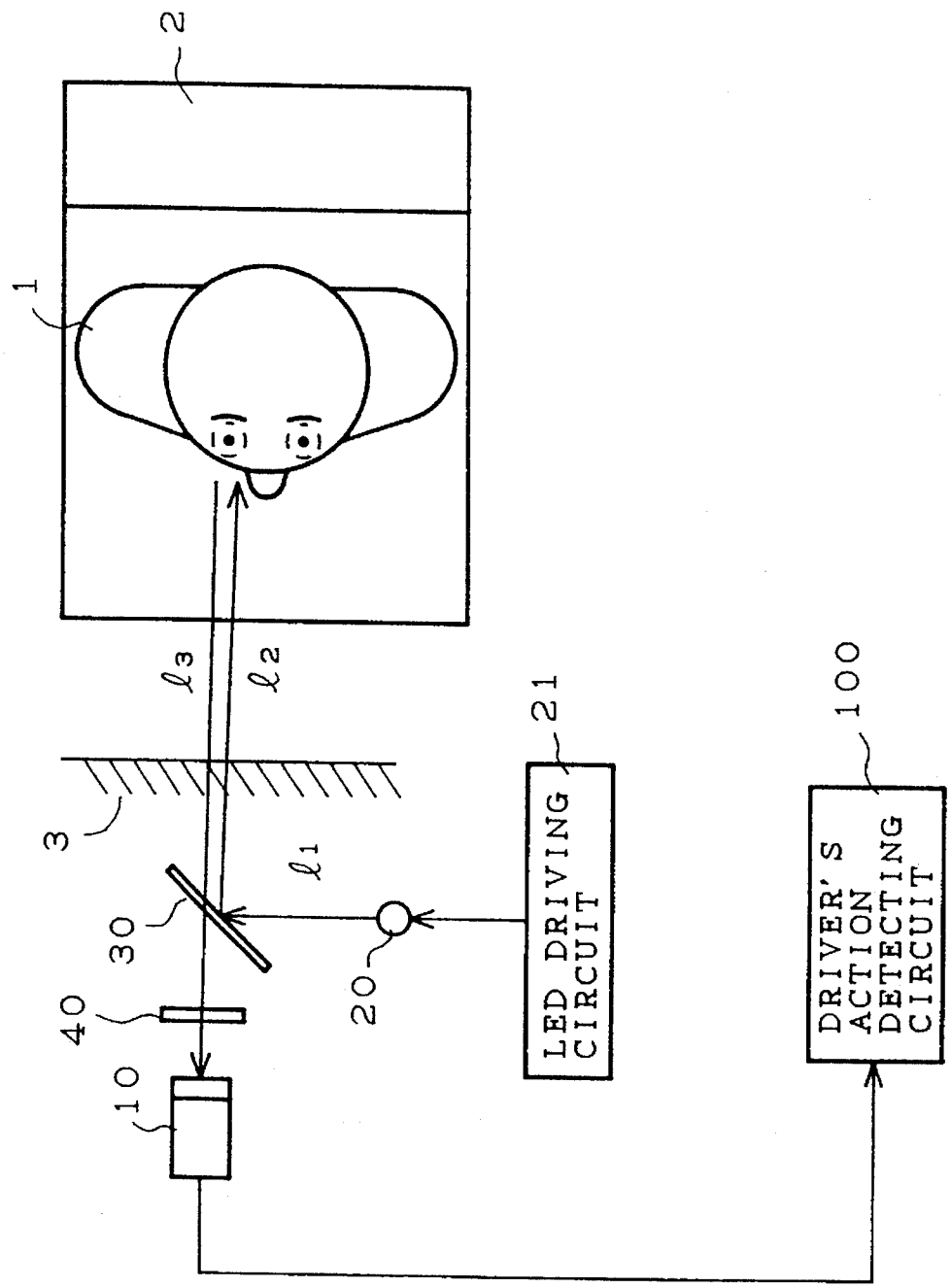
FIG. 7 is a block diagram showing the driver photographing apparatus of the embodiment 2 of the invention.
Figure 8A:
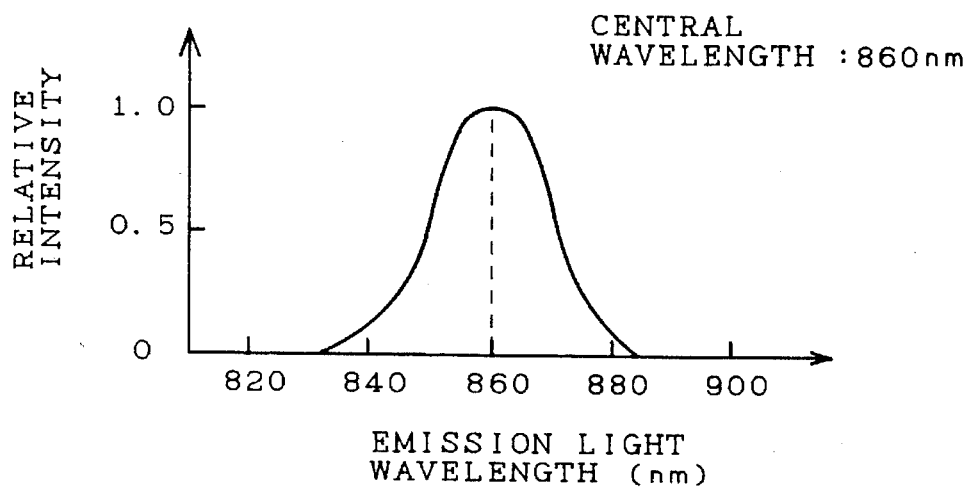
FIG. 8(a), FIG. 8(b) and FIG. 8(c) are characteristic diagrams showing each characteristic of the infrared ray LED, the BPF and the disturbance light in the embodiment 2 of the invention respectively.
Figure 8B:
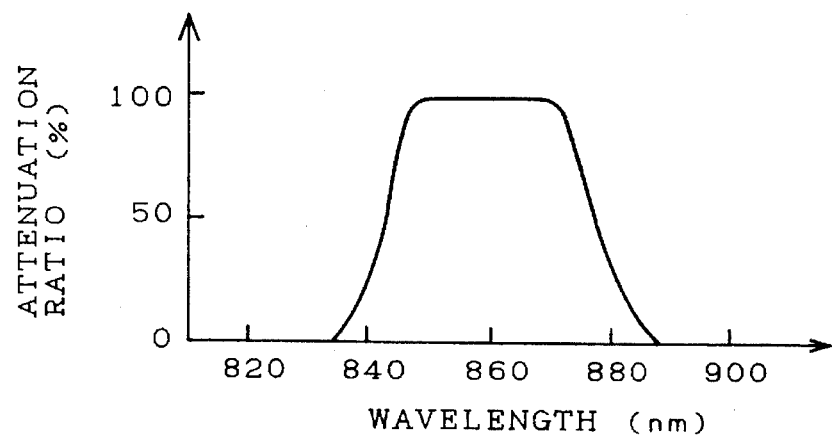

FIG. 7 is a block diagram of the driver photographing apparatus of the embodiment 2. The light emitting characteristic of the infrared ray LED 20 of FIG. 7 has a wavelength bandwidth of about 20 nm centering around 860 nm wavelength as shown in FIG. 8(a). Reference numeral 40 designates an optical band pass filter (BPF) having a passing wavelength band width of 30 nm centering around the same 860 nm wavelength as shown in FIG. 8(b). The BPF 40 is disposed in front of the CCD camera 10. The other configurations of the embodiment 2 are same as those of the embodiment 1.

Next, the operation of the embodiment 2 will be described.

Figure 8C:
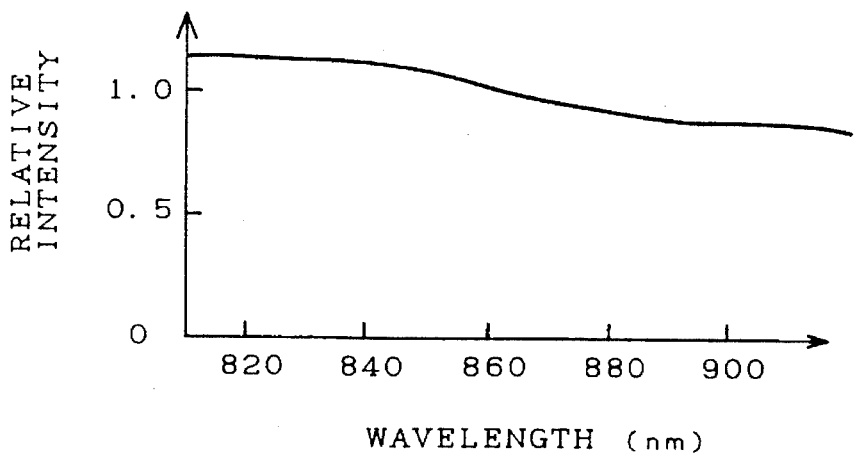

The light of the infrared ray LED 20, having the emitted light characteristic shown in FIG. 8(*a*), is reflected on the half mirror 30, similarly to the embodiment 1, to illuminate the face of the driver 1. The light forming the images of the driver 1 passes the half mirror 30 through the optical path 13 and then passes the BPF 40. Since the central wavelength of the wavelength characteristic of the BPF 40 is almost same as that of the emitted light characteristic of the LED 20, as shown in FIG. 8(*b*), almost all of the components of the light pass the BPF 40 to reach the CCD camera 10, then the CCD camera 10 takes in the light forming the images of the driver 1. On the other hand, the disturbance light owing to the sunlight has light components ranging over a wide wavelength band width as shown in FIG. 8(*c*). Almost all of the wavelength components, except for the components near 860 nm, of the light of the images of the driver 1, illuminated by the disturbance light, diminish almost completely, and consequently, only the limited components of the disturbance light are input into a CCD camera 10. As a result, the influence of the disturbance light decreases, thus the images reflected on retinas owing to the coaxially irradiating illuminating from the infrared ray LED 20 becomes capable of being observed distinctly and the images of pupils in high brightness can be obtained. The image processings after that for obtaining the centers of the pupils will be executed in the same method as those in the embodiment 1.

Moreover, in the embodiment 2, the disturbance light is attenuated by the BPF 40 and the images reflected on retinas are photographed by the CCD camera 10 having wide wavelength band width sensitivity. But, photoelectric transforming devices having sensitivity only near the emitted light wavelength of the infrared ray LED may be used without using the BPF 40.

EMBODIMENT 3.

Figure 9:
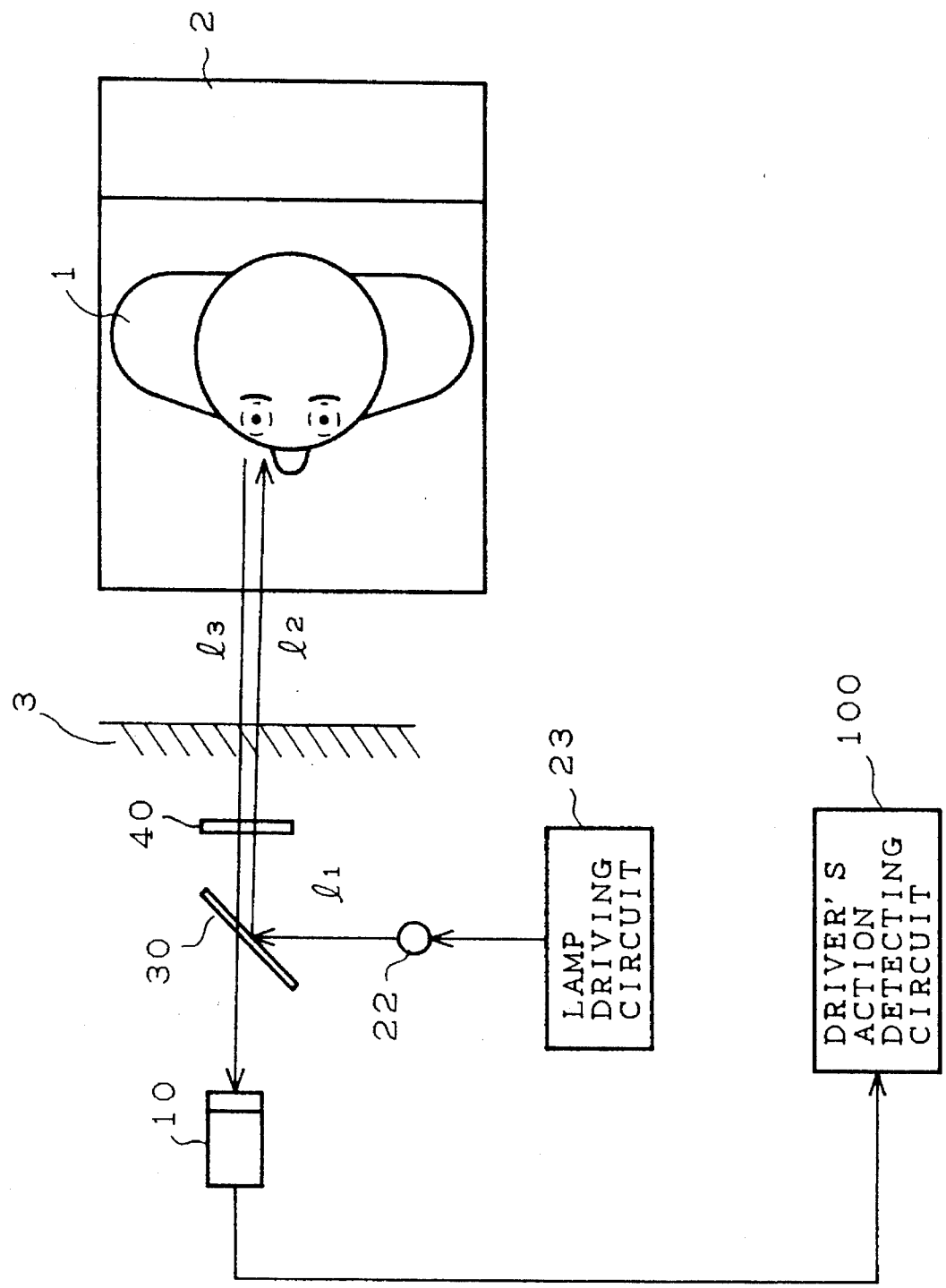
FIG. 9 is a block diagram showing the driver photographing apparatus of the embodiment 3 of the invention.

FIG. 9 is a block diagram showing the driver photographing apparatus of the embodiment 3 of the present invention. In the aforementioned embodiment 2, the infrared ray LED 20 having comparatively narrow emission light wavelength band as an illuminating means, then the embodiment 2 has a problem that the light components passing the BPF 40 become small according to temperature changing because infrared ray LEDs have specific characters that their emission light wavelengths vary in accordance with temperature. It may solve this problem to widen the wavelength band width of the BPF 40, but to widen the wavelength band width of the BPF 40 causes another problem that the suppressing effect of the disturbance light becomes smaller in proportion to make the wavelength band width wider.

In this embodiment 3, the lamp 22 having a wide emission light wavelength band (for example, a reflex lamp or an incandescent lamp) is used as the illuminating means, and the lamp 22 is driven by the lamp driving circuit 23. Moreover, the BPF 40 is disposed between the illuminating means 22 and the driver 1 and between the driver 1 and the CCD camera 10.

Next, the operation of this embodiment will be described.

Figure 10A:
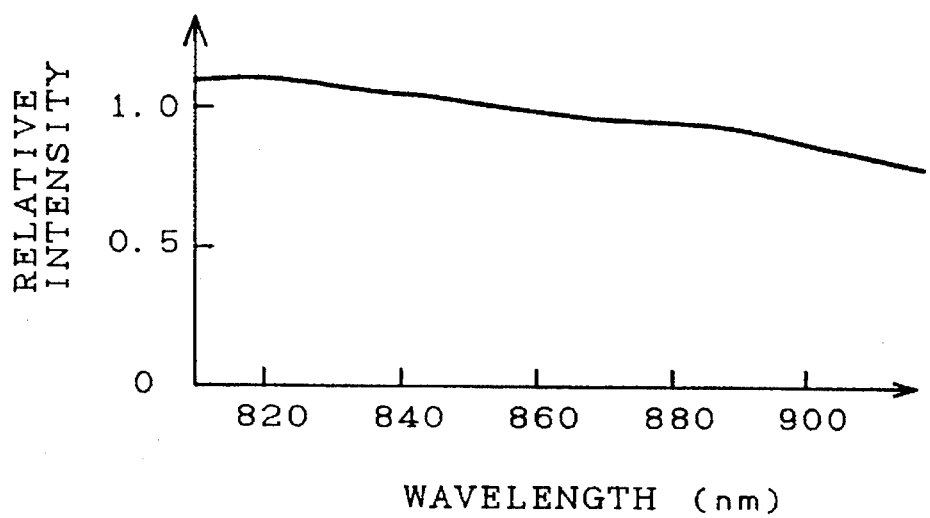
FIG. 10(a) and FIG. 10(b) are characteristic diagrams showing each characteristic of the lamp and the BPF in the embodiment 3 of the invention.
Figure 10B:
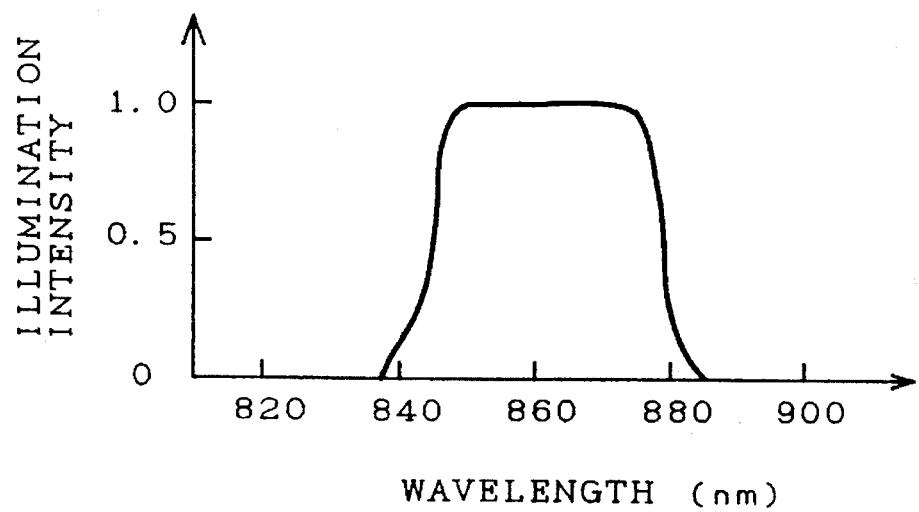

FIG. 10(*a*) is a characteristic diagram showing the emission light wavelength characteristic of the lamp 22 in the embodiment 3 of the invention. The illuminating light of the lamp 22, after passing the BPF 40, takes the wavelength characteristic of FIG. 10(*b*), such that the face illuminating light has a narrow wavelength band. The light forming the images of the face illuminated by the illuminating light again passes the BPF 40 to be input into the CCD camera 10. At this time, almost all of the light of the image passes the BPF 40. On the other hand, the wavelength band of the face image light by the disturbance light is limited by the BPF 40, such that the intensity of the image light by the disturbance light decreases. As the result, the influence of the disturbance light is attenuated, similarly to the embodiment 2, and consequently, the images reflected on retinas by means of the coaxial irradiating illumination from the lamp 22 can be observed distinctly, and the images having high brightness at pupils can be obtained.

Moreover, two BPFs having the same wavelength characteristic may be used as the BPF 40, wherein two BPFs would be respectively disposed on the optical path connecting the lamp 22 with the driver 1 and on the optical path connecting the CCD camera 10 with the driver 1.

EMBODIMENT 4.

Figure 11:
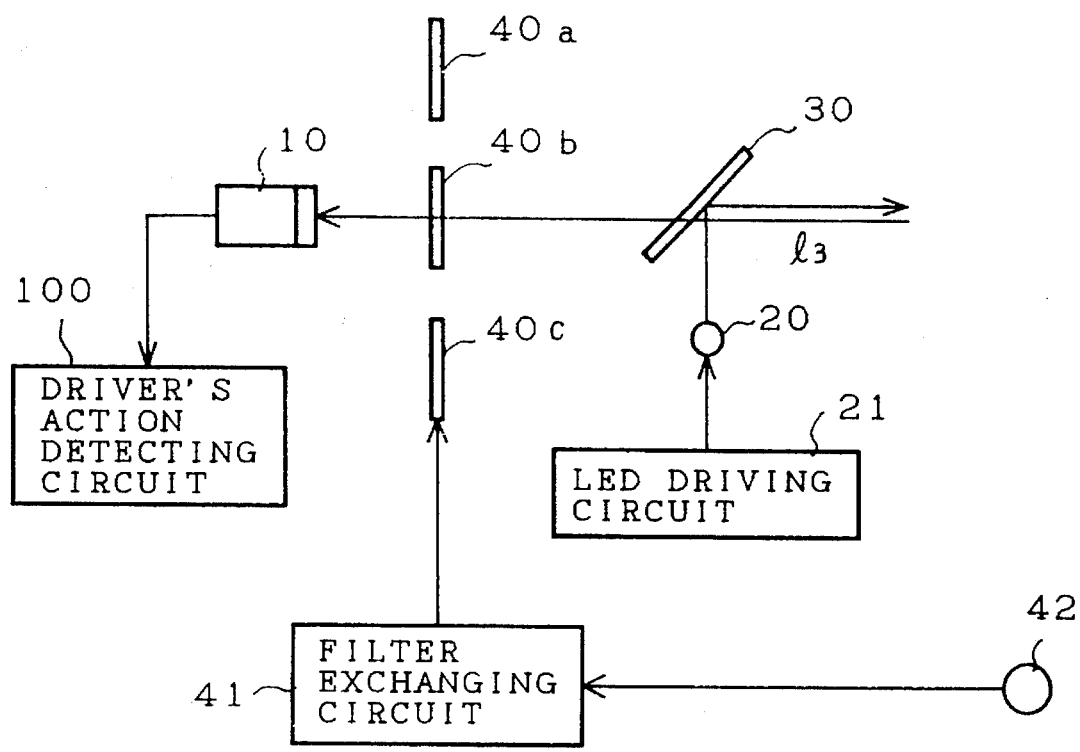
FIG. 11 is a block diagram showing the driver photographing apparatus of the embodiment 4 of the invention.
Figure 12:
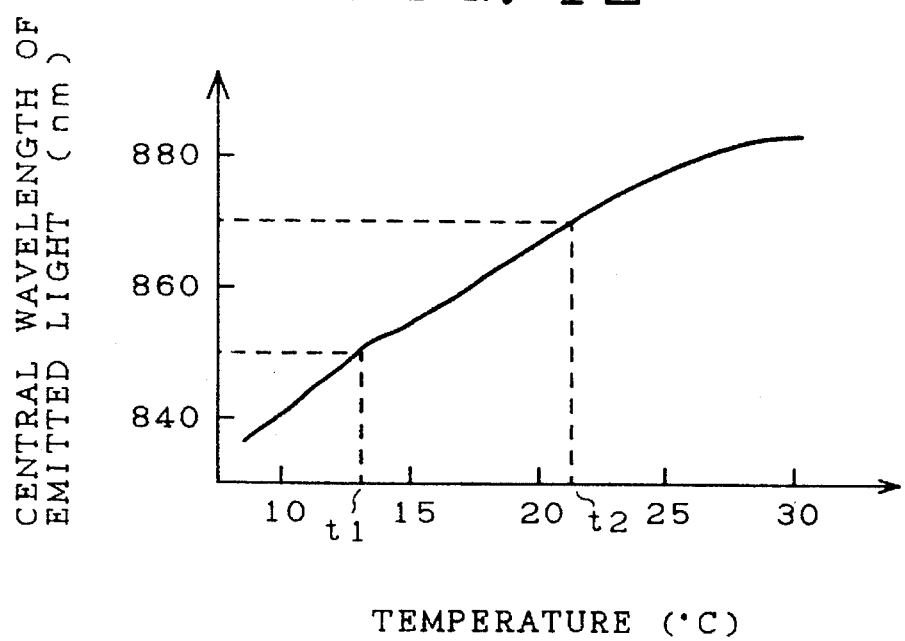
FIG. 12 is a characteristic diagram showing relation between the emitted light central wavelength of the LED and temperatures in the embodiment 4 of the invention.
Figure 13:
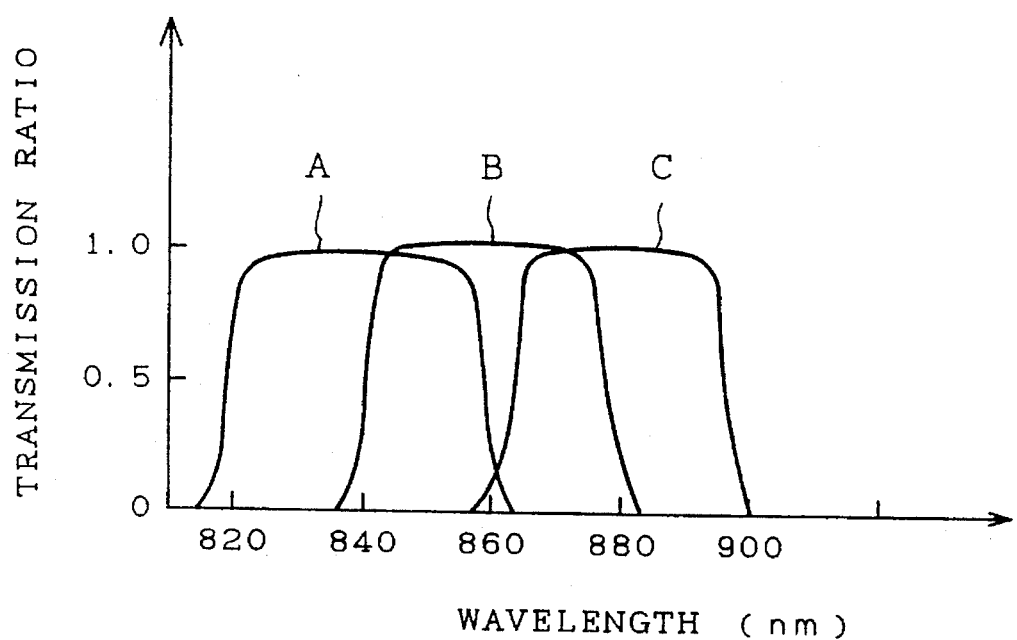
FIG. 13 is a characteristic diagram showing wavelength characteristics of the BPF in the embodiment 4 of the invention.

FIG. 11 is a block diagram showing the driver photographing apparatus of the embodiment 4 of the invention. In this embodiment 4, BPFs are equipped to account for the changing of the emission light wavelengths of the infrared ray LED 20, and they are exchanged in accordance with the changing. In FIG. 11, reference numerals 40*a*, 40*b* and 40*c* designate plural BPFs having different wavelength characteristics from one another; numeral 41 designates a filter exchanging circuit; and numeral 42 designates a temperature sensor. FIG. 12 is a characteristic diagram showing the relation between the central wavelength of the emission light of the LED 20 and temperature. The central wavelengths change in accordance with temperature as follows: 840 nm at 10° C., 865 nm at 20° C., and 885 nm at 30° C. Moreover, FIG. 13 is a characteristic diagram showing the wavelength characteristics of each BPF. The curved line A designates the wavelength characteristic of the BPF 40*a*; the curved line B designates the wavelength characteristic of the BPF 40*b*; and the curved line C designates the wavelength characteristic of the BPF 40*c*. The central wavelength of the BPF 40*a* is 840 nm; the central wavelength of the BPF 40*b* is 860 nm; and the central wavelength of the BPF 40*c* is 880 nm.

Next, the operation of the embodiment 4 will be described.

In this embodiment 4, the temperature sensor 42 detects temperature, and the filter exchanging circuit 41 controls the exchanging of the BPFs 40*a*, 40*b*, 40*c* disposed on the optical path 13 as follows: the BPF 40*a* is used at the temperature of 13° C. and below; the BPF 40*b* is used at the temperature from 13°–21°C.; and the BPF 40*c* is used at the temperature of 21° C. and over. The operation after that is same as that of the embodiment 2. As stated above, the images reflected on retinas can be obviously photographed by exchanging the BPFs according to temperature, even if emitted light wavelengths change.

EMBODIMENT 5.

In the above mentioned embodiment 4, the BPFs are exchanged in accordance with detected temperature. But, it may be applicable to detect the emission light wavelength of the LED 20 by providing a group of photoelectric transforming devices having different wavelength sensitivity from one another in place of the temperature sensor 42, and to exchange the BPFs so that the BPF, whose wavelength characteristic has a central wavelength near the detected emitted light wavelength by the photoelectric transforming devices, is disposed on the optical path 13. By means of such a configuration, the images reflected on retinas can be obviously photographed if the emitted wavelengths of the LED vary owing to primary factors other than temperature.

EMBODIMENT 6.

Figure 14:
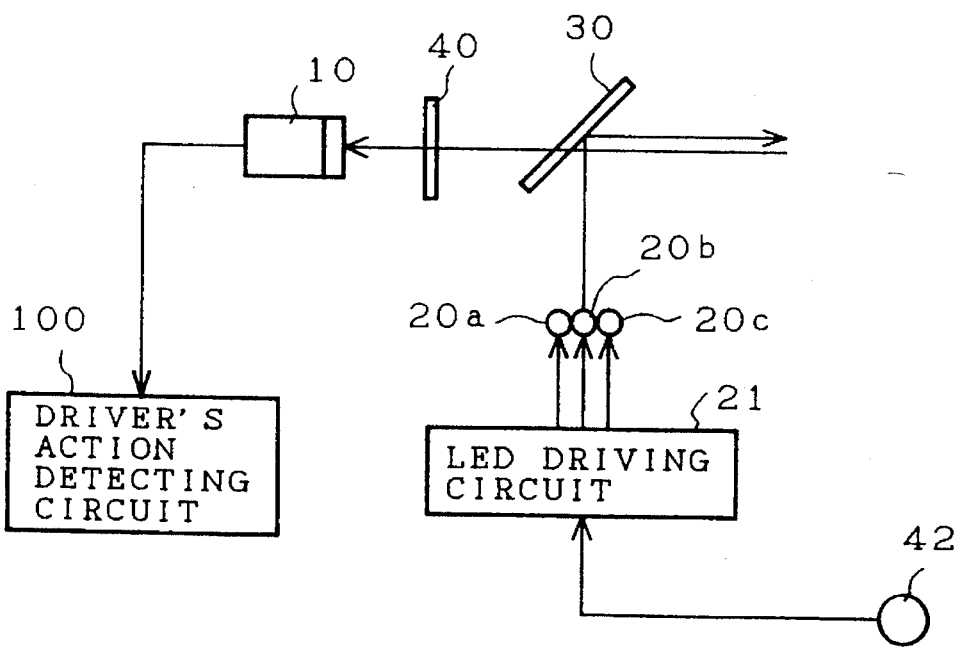
FIG. 14 is a block diagram showing the driver photographing apparatus of the embodiment 6 of the invention.
Figure 15:
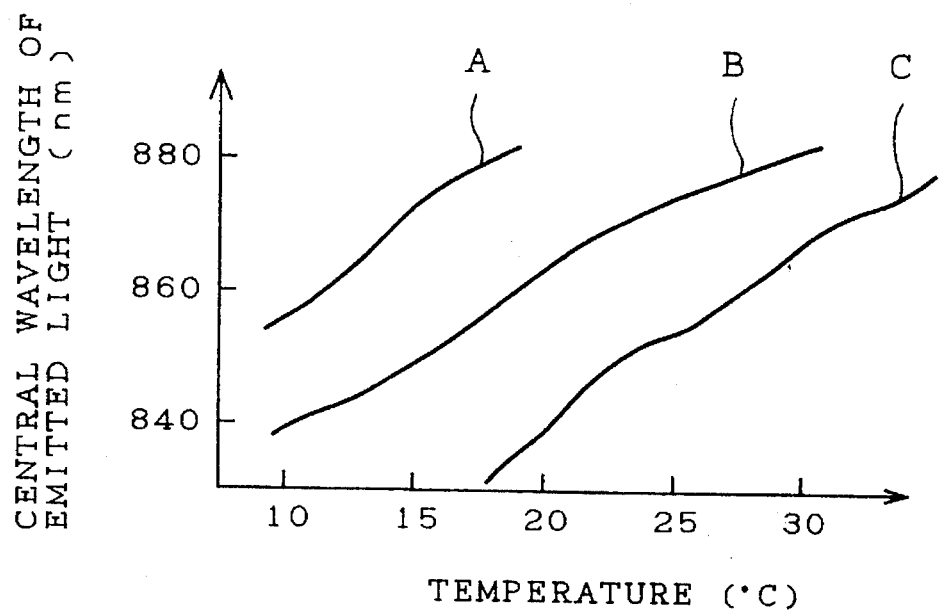
FIG. 15 is a characteristic diagram showing relation between the emitted light central wavelength of the LED and temperatures in the embodiment 6 of the invention.

FIG. 14 is a block diagram showing the driver photographing apparatus of the embodiment 6 of the invention. In this embodiment 6, plural LEDs having different emission light central wavelengths from one another are installed and exchanged in accordance with temperature as compensation for the changing of the emission light wavelengths of the infrared ray LED. In FIG. 14, reference numerals 20a, 20b and 20c designate plural LEDs having different emission light central wavelengths from one another. FIG. 15 is a characteristic diagram showing the relation between the emission light central wavelengths of each of the LEDs 20a, 20b, 20c and temperature. The curved line A designates the temperature characteristic of the LED 20a; the curved line B designates the temperature characteristic of the LED 20b; and the curved line C designates the temperature characteristic of the LED 20c. Moreover, the BPF 40 is an optical BPF having a 30 nm wavelength band width, whose central wavelength is 860 nm, being disposed in front of the CCD camera 10, similarly to that in the embodiment 2.

Next, the operation of the embodiment 6 will be described.

In this embodiment 6, the temperature sensor 42 detects temperature, and the LED driving circuit 21 controls the application of LEDs as follows: the LED 20a is used at the temperature of 15° C. and below; the LED 20b is used at the temperature between 15° C. through 23° C.: and the LED 20c is used at the temperature of 23° C. or more. By exchanging the LEDs according to temperature in such a way, images reflected on retinas are obviously photographed even if the emission light wavelengths changes.

EMBODIMENT 7

Figure 16:
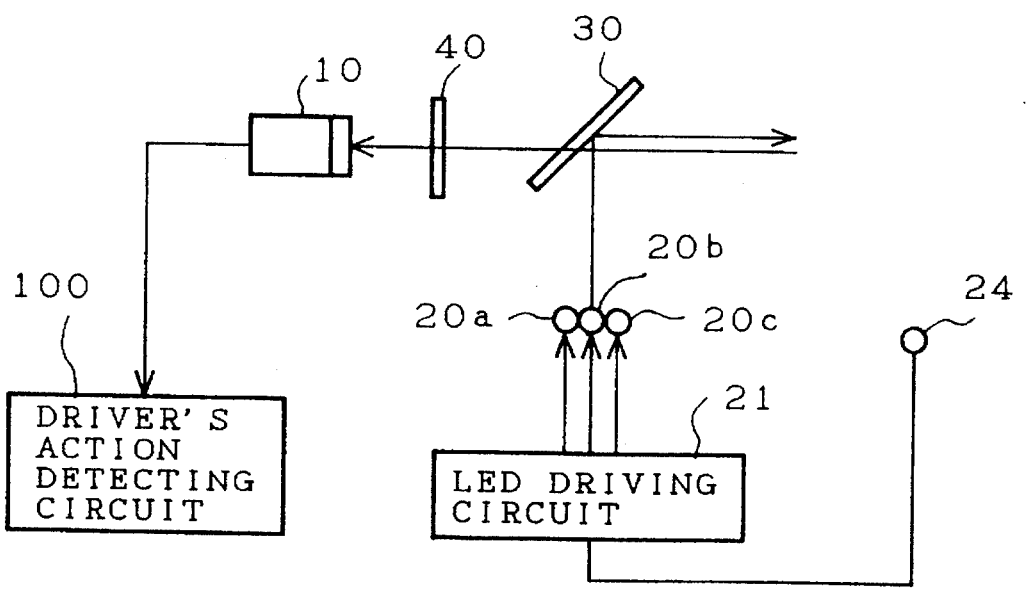
FIG. 16 is a block diagram showing the driver photographing apparatus of the embodiment 7 of the invention.

Though the LEDs are exchanged in accordance with the detected temperature in the aforementioned embodiment 6, it may be applicable to install a photoelectric transforming device 24, as shown in FIG. 16, having its sensitivity at the same 860 nm wavelength as that of the BPF 40, instead of the temperature sensor 42, and to detect the optical power of each of the LEDS 20a, 20b and 20c, and to select the LED showing the largest power, and further to exchange the LEDs so as to select the LED showing the largest power. By taking such a configuration, the images reflected on retinas can be obviously photographed if the emission wavelengths of the LEDs vary owing to primary factors other than temperature.

EMBODIMENT 8.

The influence of the shifting of the emission light central wavelength of the LED is compensated for by providing the plural BPFs or plural LEDs in each embodiment mentioned above, but it may applicable to cool or warm the LED by using an air conditioner installed in a car without shifting the central wavelength according to the changing of temperature.

EMBODIMENT 9.

Figure 17:
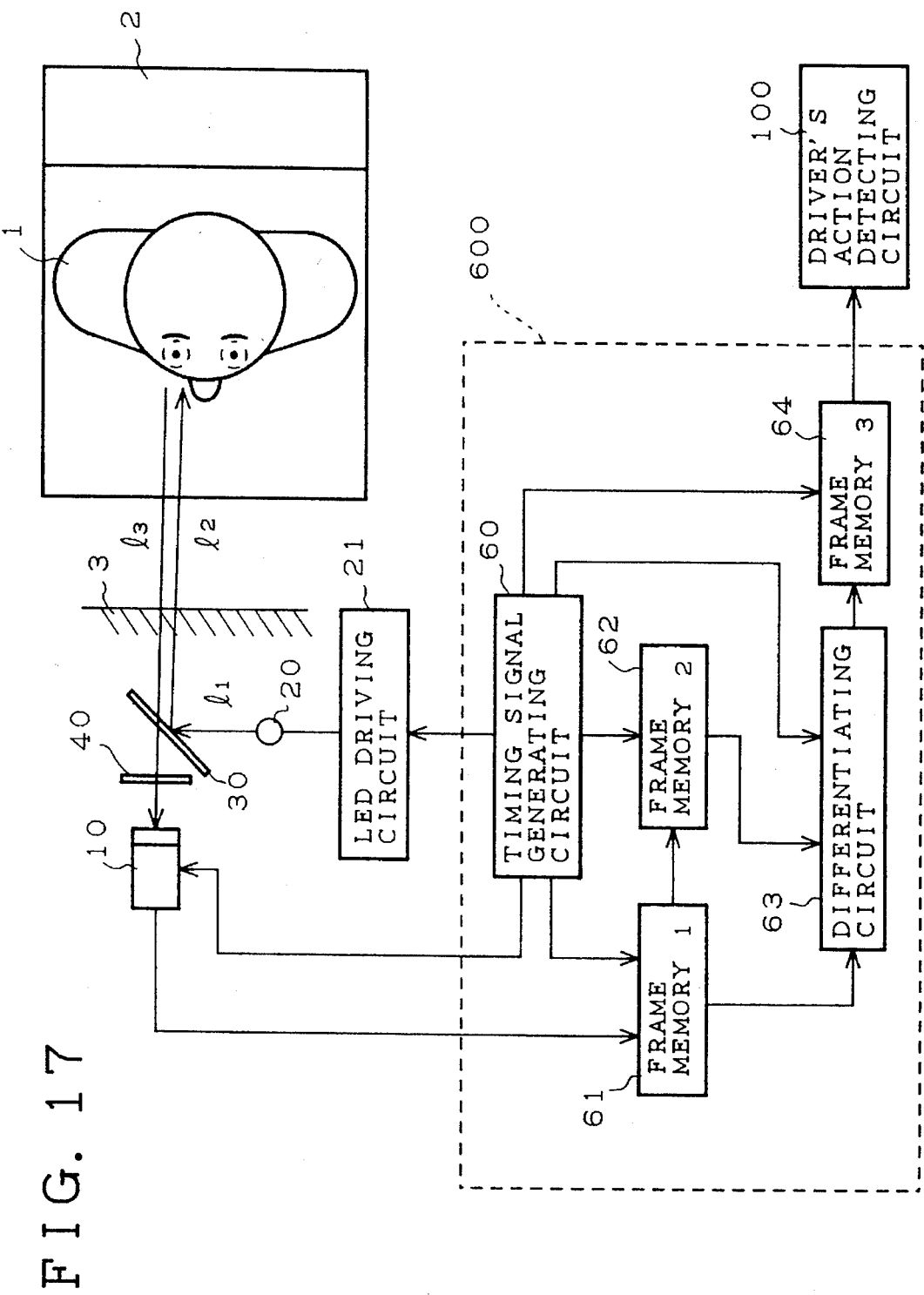
FIG. 17 is a block diagram showing the driver photographing apparatus of the embodiment 9 of the invention.
Figure 18:
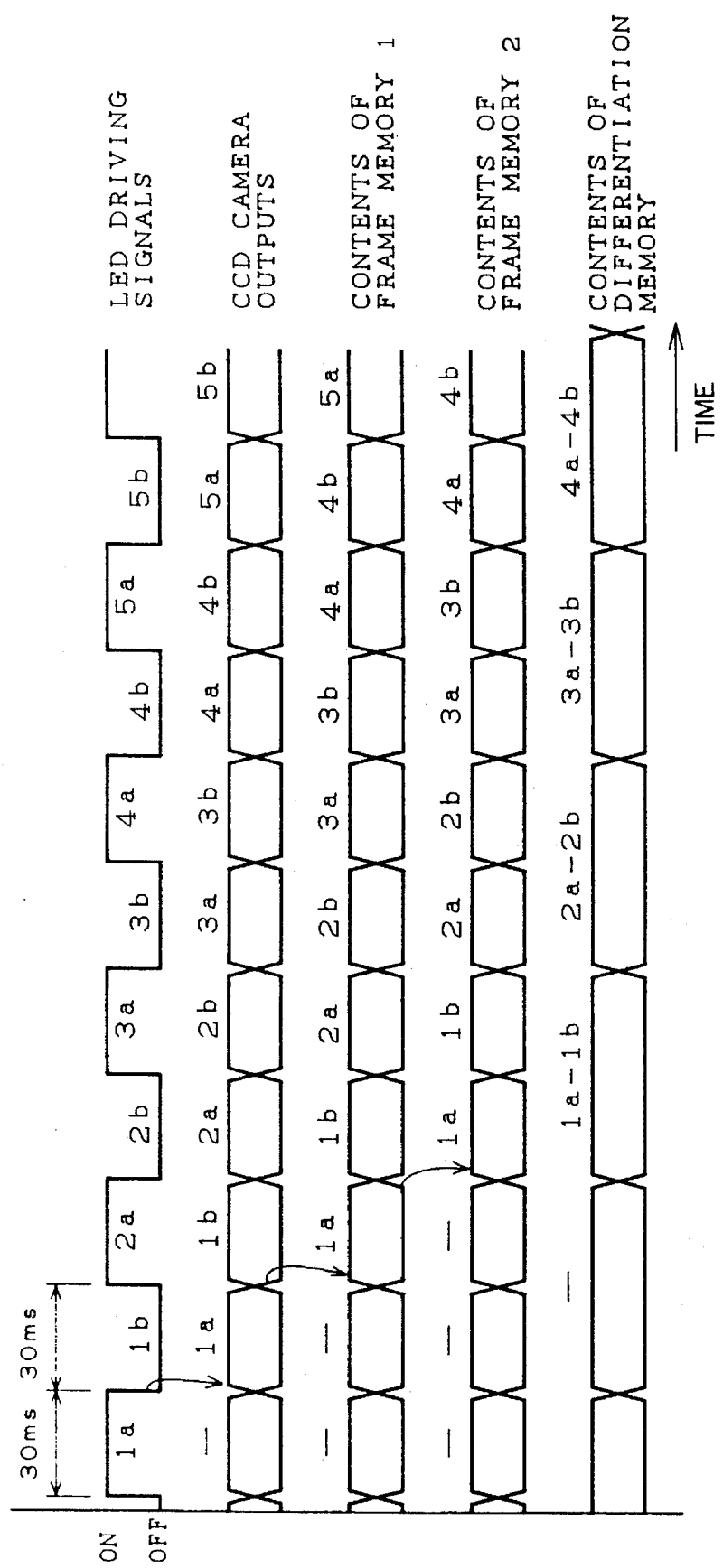
FIG. 18 is a timing chart for explaining the operation of the driver photographing apparatus of the embodiment 9 of the invention.

In the aforementioned embodiments 2 through 8, the images reflected on retinas can be obviously photographed in cloudy weather. However, there is a problem that pupils cannot be contrasted brightly enough in comparison with the images reflected from cheeks and the like. In this embodiment 9, the influence of the disturbance light is further removed by signal processing techniques. FIG. 17 shows the configuration of this embodiment. In FIG. 17, reference numeral 60 designates a timing signal generating circuit; numeral 61 designates a frame memory 1; numeral 62 designates a frame memory 2; numeral 63 designates a differentiating circuit; numeral 64 designates a frame memory 3; and the timing signal generating circuit 60, the frame memory 1 (61), the frame memory 2 (62), the differentiating circuit 63 and the frame memory 3 (64) constitute an image processing means 600. FIG. 18 is a timing chart for explaining the operation of the driver photographing apparatus of the embodiment 9 of the invention. The timing signal generating circuit 60 generates timing signals, for example, every 30 milliseconds. The LED driving circuit 21 generates LED driving signals for repeating turning on or off the LED 20 every 30 milliseconds in conformity with the timing signals from the aforementioned timing signal generating circuit 60. The CCD camera 10 photographs one picture every 30 milliseconds in conformity with the timing signals from the timing signal generating circuit 60. Such that the face images at instances when the LED 20 emits light and the face images at instances when the LED 20 does not emit light are generated one after the other. The frame memories 1, 2 and 3 are memories for memorizing the data of one picture respectively. The image data memorized in the frame memory 1 are transferred to the frame memory 2 every frame. Consequently, the frame memory 2 always memorizes the image data of the frame memory 1 at the previous 30 milliseconds. That is to say, if the image data of the frame memory 1 are the data when the LED 20 is turned on, the image data of the frame memory 2 is the data when the LED 20 is turned off. After the next 30 milliseconds, the image data are reversed. The differentiating circuit 63 differentiates between the image data of the frame memory 1 and the frame memory 2 when the frame memory 1 has memorized the image data at the time when the LED 20 was turned on. In this case, the face image data outputted from the differentiating circuit 63 are the image data of subtracting (the image data illuminated by disturbance light) from (the image data illuminated by the disturbance light and the light from the LED 20). Then the face image data illuminated only by the illuminating light from the infrared ray LED can be obtained in the frame memory 3 as the result. Because the image data have removed the influence of the disturbance light by means of the signal processing, the images where the brightness of pupils are high are obtained every 60 milliseconds.

EMBODIMENT 10.

Figure 19:
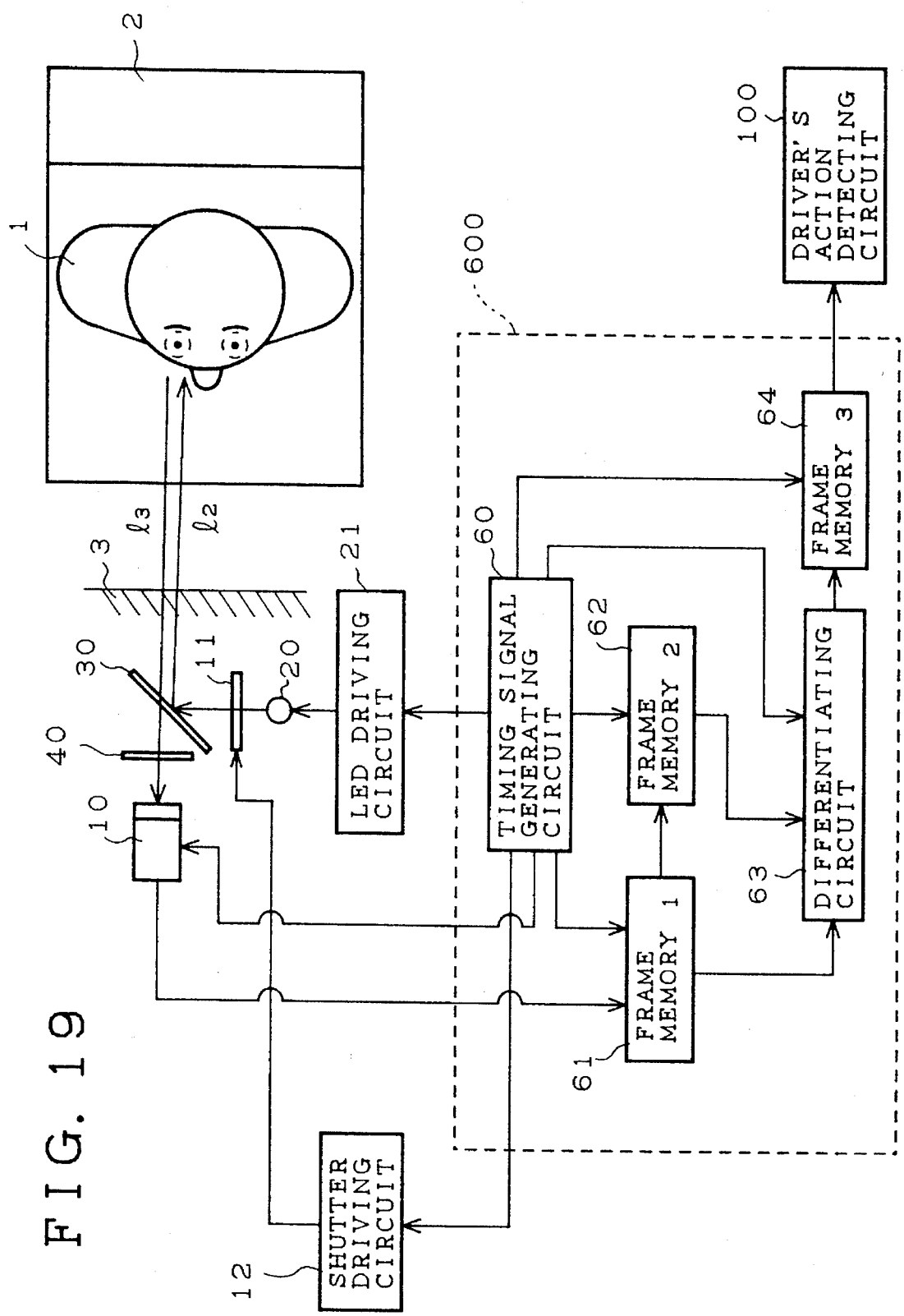
FIG. 19 is a block diagram showing the driver photographing apparatus of the embodiment 10 of the invention.
Figure 20:
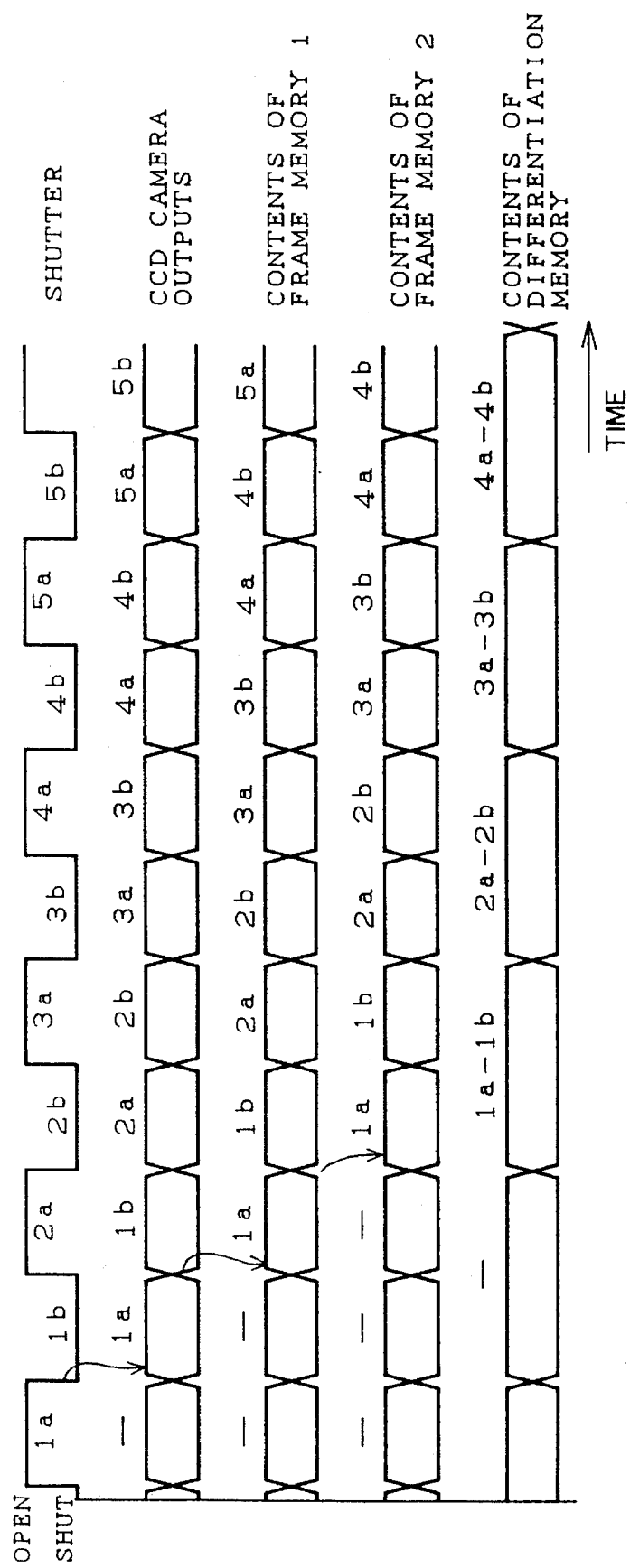
FIG. 20 is a timing chart for explaining the operation of the driver photographing apparatus of the embodiment 10 of the invention.

In the aforementioned embodiment 9, the LED 20 turns on and off alternately in accordance with LED driving signals for driving the LED 20, but it also may be applicable to control the LED's turning on or off by means of opening or shutting a shutter intercepting the illuminating light from the LED 20. FIG. 19 is a block diagram showing the driver photographing apparatus of the embodiment 10 of the invention. In FIG. 19, reference numeral 11 designates a shutter realized, for example, by a liquid crystal shutter. Numeral 12 designates a shutter driving circuit. FIG. 20 is a timing chart for explaining the operation of the driver photographing apparatus of the embodiment 10. The shutter driving circuit 12 generates signals for repeating the shutter's opening and shutting, for example, every 80 milliseconds, in accordance with the timing signals from the timing signal generating circuit 60. The operation of the embodiment 10 other than the operation described above is the same as that of the embodiment 9.

EMBODIMENT 11.

Though the period of the LED's turning on and off is made to be 30 milliseconds and the image signals are outputted to the driver's action detecting circuit 100 every 60 milliseconds in the aforementioned embodiments 9 and 10, the period is not restricted to 30 milliseconds. For example, it may be applicable to set the period of the LED's turning on and off to 15 milliseconds, and to set the camera's signal outputting period to 15 milliseconds, and further to set the signal outputting period from the frame memory 3 to 30 milliseconds.

EMBODIMENT 12.

Figure 21:
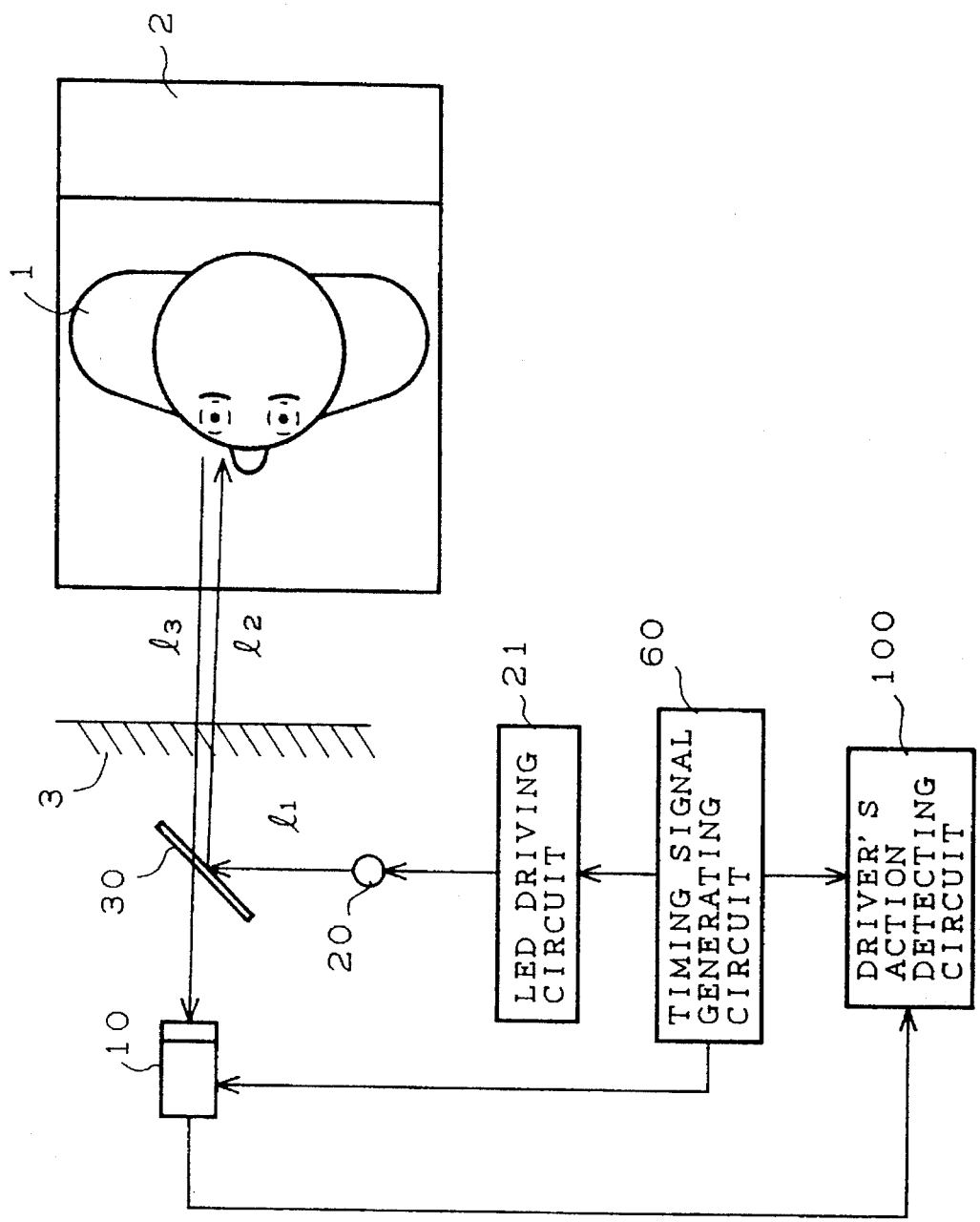
FIG. 21 is a block diagram showing the driver photographing apparatus of the embodiment 12 of the invention.
Figure 22:
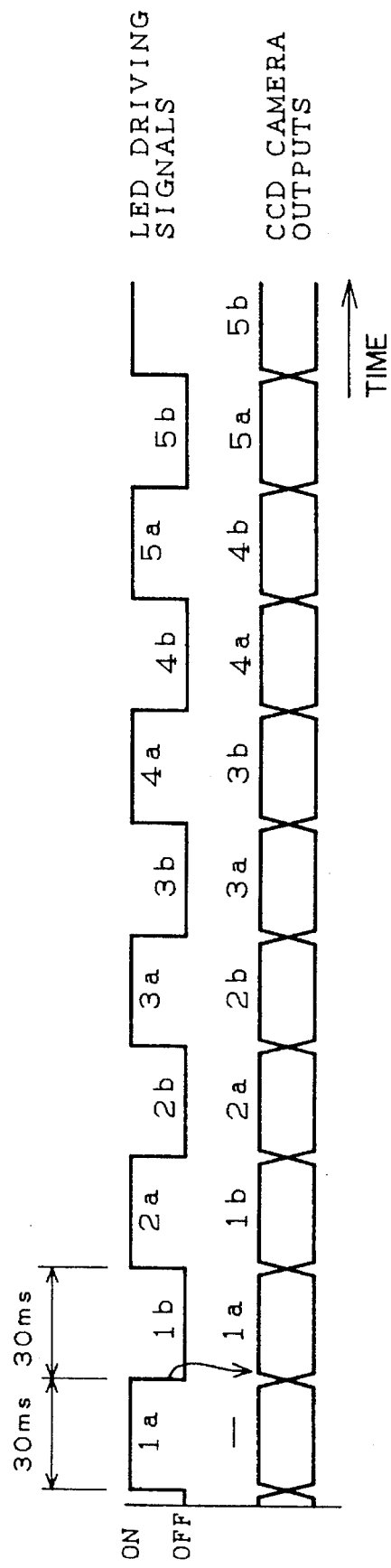
FIG. 22 is a timing chart for explaining the operation of the driver photographing apparatus of the embodiment 12 of the invention.

Though the embodiments 9, 10 carry out the differentiation via the frame memories, it may be applicable to transmit the image data to the driver's action detecting circuit 100 once and generate the differential image data by means of processing in conformity with the software in the driver's action detecting circuit 100. FIG. 21 is a block diagram showing the driver photographing apparatus of the embodiment 12 of the invention, and FIG. 22 is a timing chart for explaining the operation of the embodiment 12. In FIG. 21 and FIG. 22, the LED driving circuit 21 generates LED driving signals for repeating the LED's turning on and off in accordance with the timing signals from the timing signal generating circuit 60. The CCD camera 10 generates one picture signal, for example, every 30 milliseconds in accordance with the timing signals from the timing signal generating circuit 60. As the result, the face image signals at the time when the LED 20 emits light and the face image signals at the time when the LED 20 does not emit light are alternatively generated. In this embodiment 12, the driver's action detecting circuit 100 operates the differential image signals between both the aforementioned image signals, and the face images only by means of the illuminating light from the infrared ray LED 20 are obtained similarly as in embodiment 9.

Though the differential image signals are always operated to obtain the face images in the driver's action detecting circuit 100 in this embodiment 12, it may be applicable to obtain the face image signals by differentiating between the image signals at the time when the illuminating light exists and the image signals at the time when the illuminating light does not exist in the daytime similarly to the embodiment 12, and to obtain the face image signals by means of the image signals alone at the time when the illuminating light exists in the nighttime. Consequently, the image processings become simple. Moreover, the discrimination of the daytime and the nighttime may be done by means of a luminous intensity sensor or car headlight turning on signals and turning off signals.

Besides, not only the images reflected on retinas are obtained from the differential images in the daytime in the driver's action detecting circuit 100, but also other information of the face may be obtained by the use of image signals in case the illuminating light does not exist.

EMBODIMENT 13.

Figure 23:
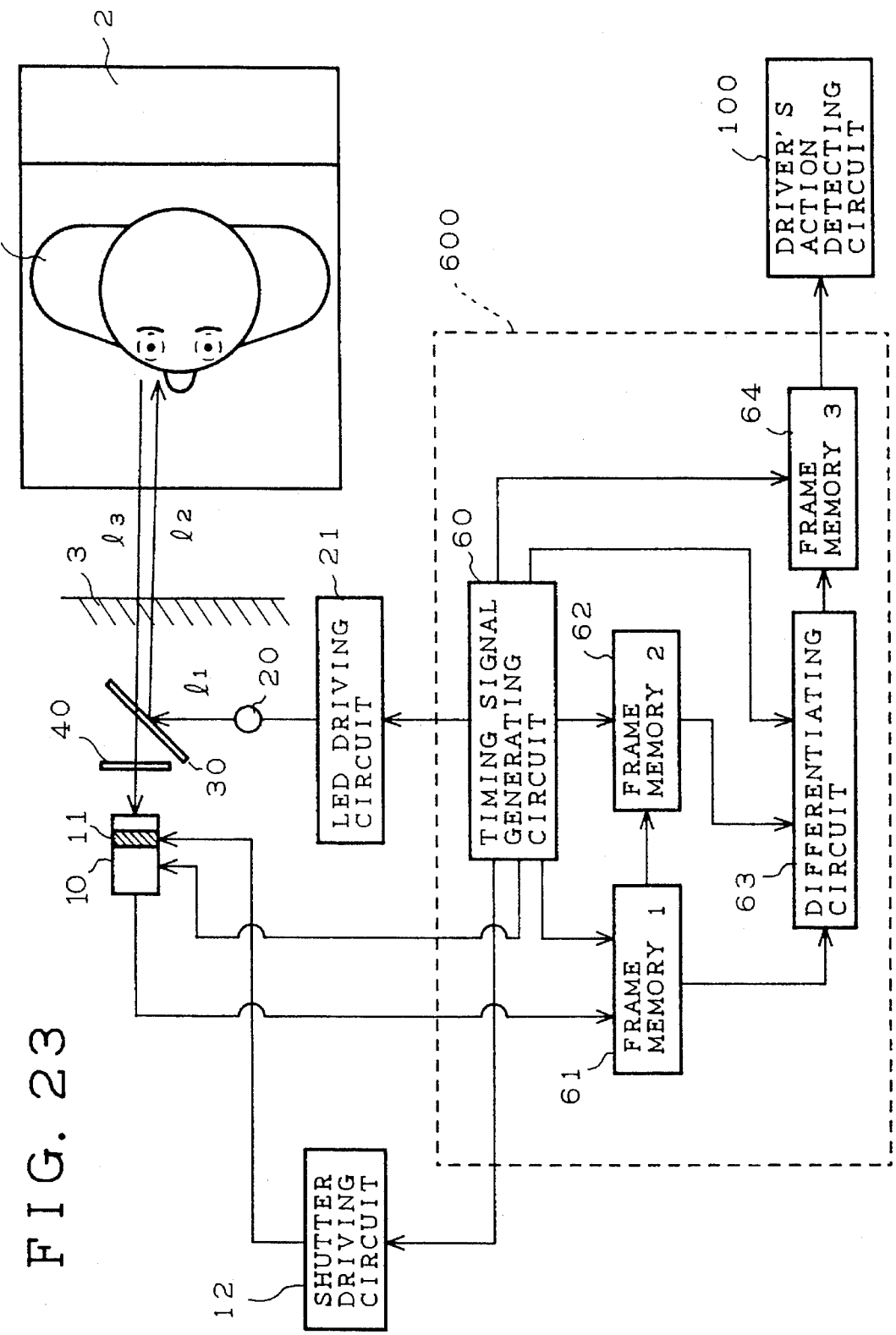
FIG. 23 is a block diagram showing the driver photographing apparatus of the embodiment 13 of the invention.
Figure 24:
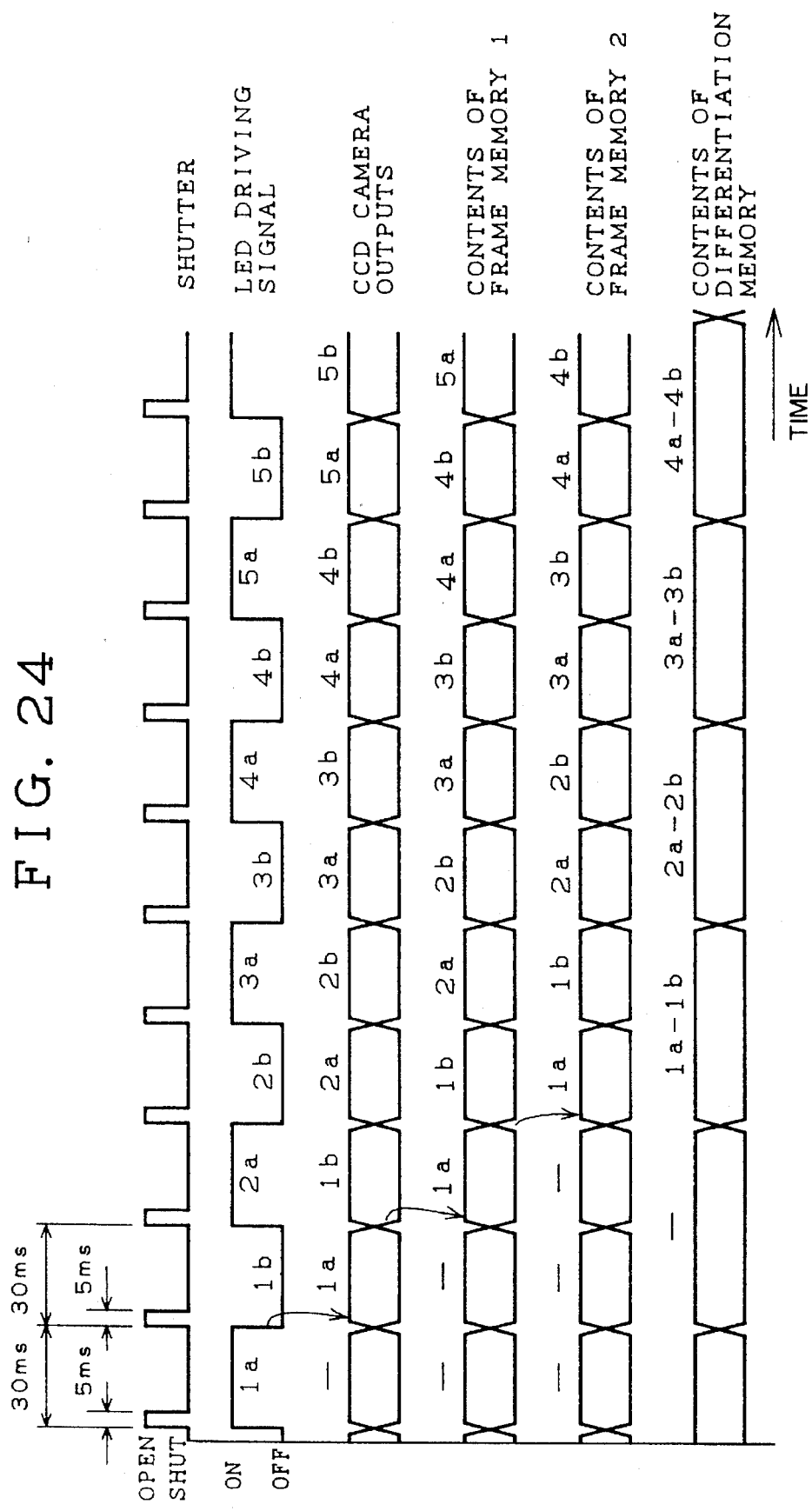
FIG. 24 is a timing chart for explaining the operation of the driver photographing apparatus of the embodiment 13 of the invention.

Though the light emitting timing of the LED 20 is set to be every 30 milliseconds in the embodiment 9 mentioned above, the shorter the interval of taking images in, the better it will be, considering the case where the eyes of a driver move rapidly. Though the time interval of taking images in is 30 milliseconds in the embodiment 9, it may be applicable to take the images at the time when the LED 20 is on and the images at the time when the LED 20 is off during shorter time period by means of the CCD camera 10 provided with a liquid crystal shutter 11. FIG. 23 is a block diagram showing the driver photographing apparatus of the embodiment 13 of the invention, and FIG. 24 is a timing chart for explaining the operation of the embodiment 13. In FIG. 23 and FIG. 24, the LED driving circuit 21 generates LED driving signals repeating turning on and off the LED 20, for example, every 30 milliseconds in accordance with the timing signals from the timing signal generating circuit 60. The shutter driving circuit 12 generates signals opening the shutter 11 for 5 milliseconds every 30 milliseconds in accordance with the turning on and off of the LED 20 according to the timing signals from the timing signal generating circuit 60 as shown in FIG. 24. The operation after that is identical to that of the embodiment 9. But, since the shutter 11 of the CCD 10 is opened for only 5 milliseconds, as shown in FIG. 24, in conformity with the turning on and off of the LED 20 in the embodiment 9, the time interval for taking each image can be shortened, then images having little blurring can be obtained even if the movement of a face is rapid.

Also, the shutter release time is not restricted to 5 milliseconds, and any release time within 30 milliseconds will do in this embodiment 13.

EMBODIMENT 14.

Figure 25:
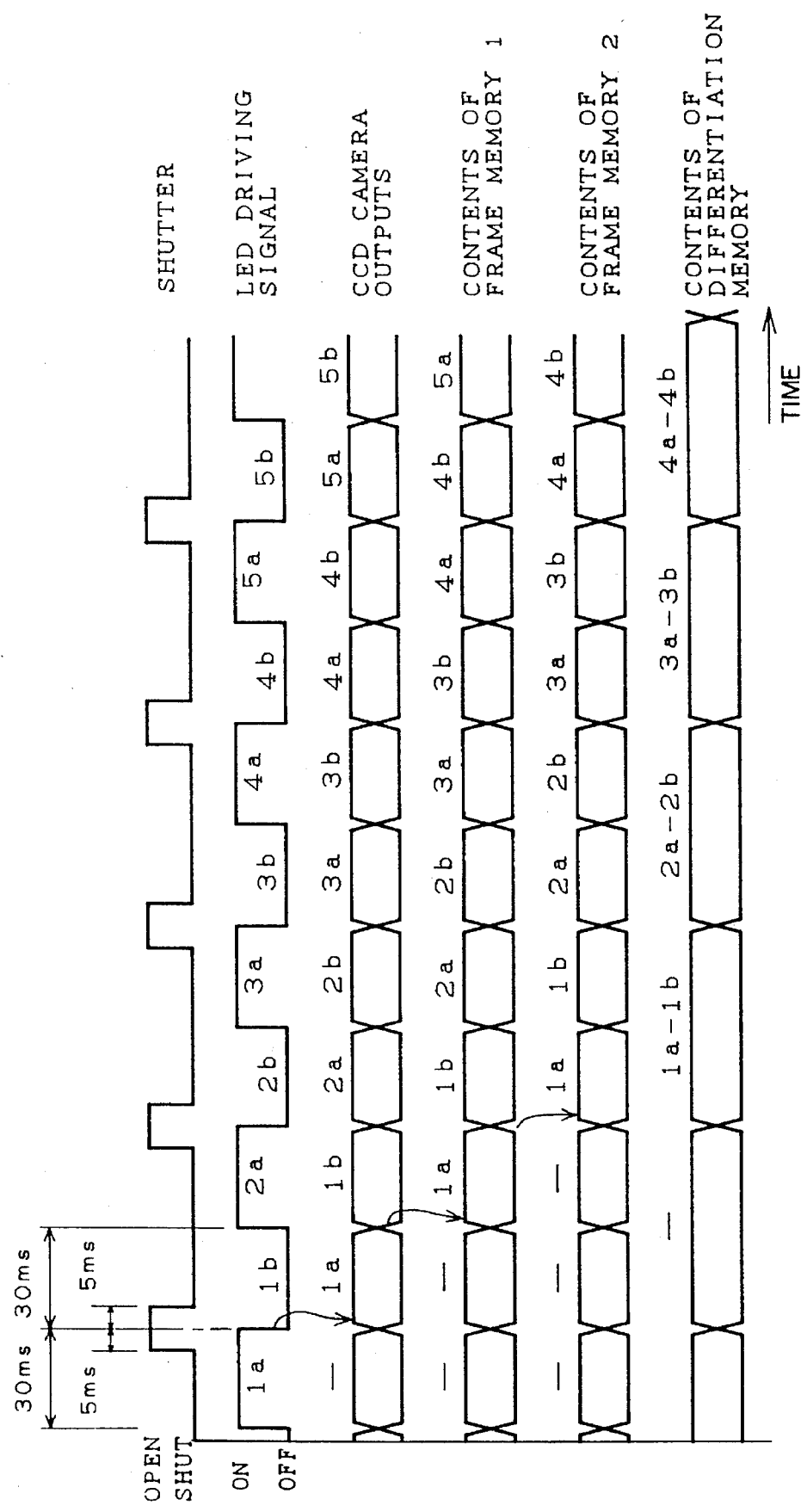
FIG. 25 is a timing chart for explaining the operation of the driver photographing apparatus of the embodiment 14 of the invention.

Moreover, considering the case where the eyes of a driver moves further rapidly than in the embodiment 13, it is preferable that the time difference between the time taking in the images in case that the LED 20 is on and the time taking in the images in case that the LED) 20 is off is small, then the difference owing to the existence of illuminating light appears in the obtained differential images. FIG. 25 is a timing chart for explaining the operation of such an embodiment of the invention. In FIG. 25, the shutter driving circuit 12 generates signals opening the shutter 11, for example, for 10 milliseconds extending over the on-state and the off-state of the LED) 20 every 60 milliseconds in conformity with the timing signals from the timing signal generating circuit 60. The operation after that is identical to that of the aforementioned embodiment 9. But, since the shutter 11 of the CCD camera 10 opens only for 5 milliseconds in accordance with the on-state of the LED 20 as shown in FIG. 25 and the shutter 11 of the CCD camera 10 continuously opens for next 5 milliseconds in conformity with the off-state of the LED in this embodiment, the difference between the time spent taking in the images when the LED 20 is on and the time spent taking in the images when the LED 20 is off can be made to be 5 milliseconds in this embodiment as compared with 30 milliseconds in the embodiment 9 and 13. As a result of this, the difference due to the existence of illuminating light can be caught more obviously in the obtained difference images, then images having little blurring can be obtained even if the movement of a face is rapid.

EMBODIMENT 15.

Moreover, the shutter 11 is provided in front of the LED 20 and the shutter 11 is opened and shut in accordance with the turning on and off of LED 20 in the embodiment above mentioned, but it may be applicable to control the light input electrically by means of devices having selecting function of taking in images or not at a certain time, for example a Charge Injection Device (CID), instead of the shutter 11.

EMBODIMENT 16.

Figure 26:
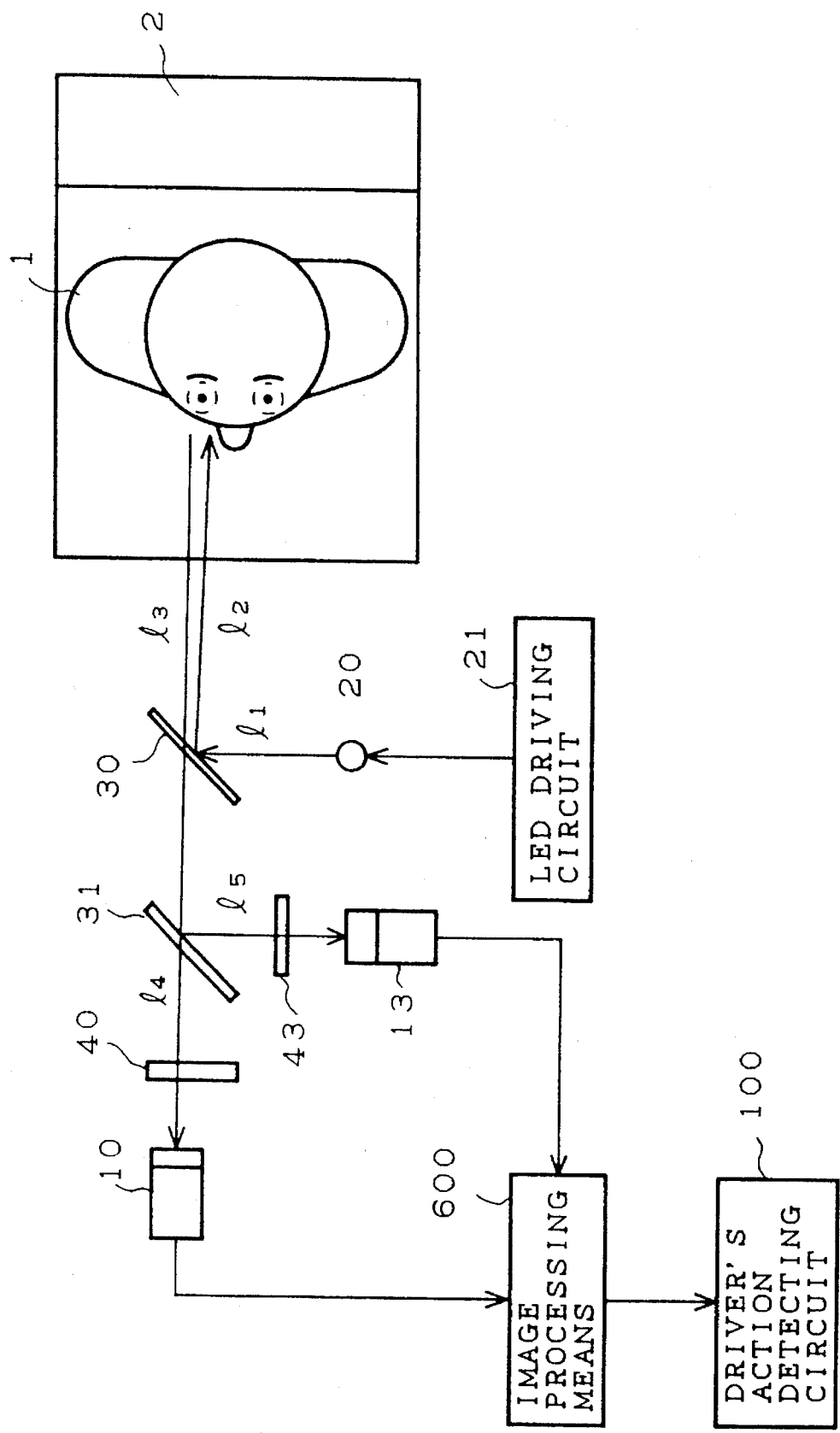
FIG. 26 is a block diagram showing the driver photographing apparatus of the embodiment 16 of the invention.
Figure 27:
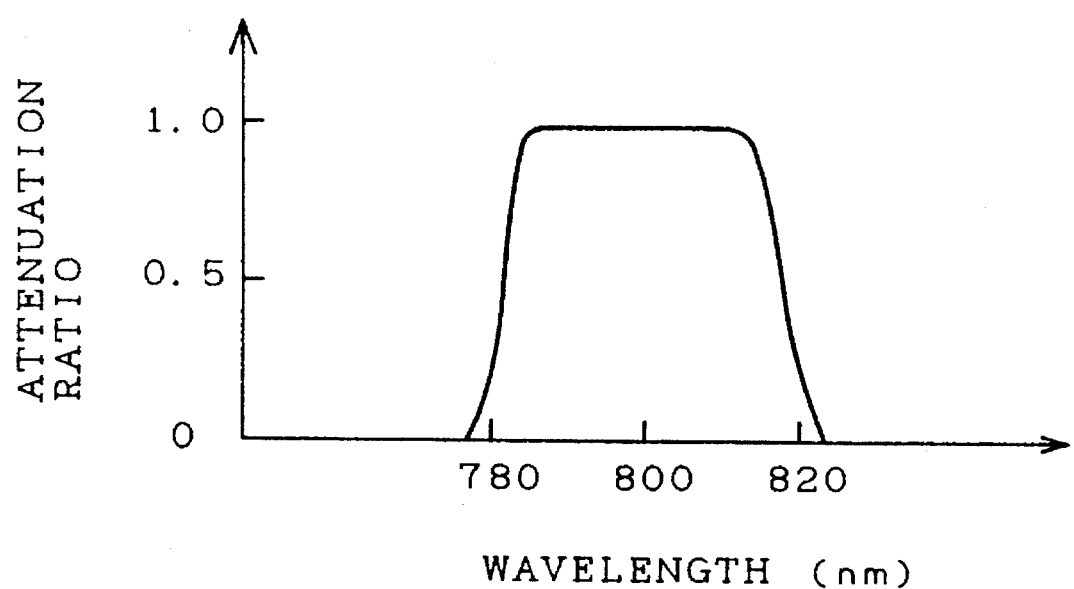
FIG. 27 is a characteristic diagram showing the wavelength characteristic of the second BPF in the embodiment 16 of the invention.

FIG. 26 is a block diagram showing the driver photographing apparatus of the embodiment 16 of the invention. In FIG. 26, reference numeral 13 designates a CCD camera; and numeral 43 designates an optical BPF (the second BFF) having a 30 nm wavelength band width around the 800 nm central wavelength as shown in FIG. 27, the wavelength characteristic of which BPF is different from the BPF 40 (the first BPF) (the wavelength characteristic shown in FIG. 8(*b*): the central wavelength of which is 860 nm). Reference numeral 600 designates an image processing means.

Next, the operation of the embodiment 16 will be described.

The light emitted from the infrared LED 20 having the light emitting characteristic shown in FIG. 8(*a*) is reflected by the half mirror 30 to irradiate the face of the driver 1. The light forming images of the driver 1 from the LED 20 passes through the half mirrors 30, 31 through the optical paths 13, 14. Then, almost all of the light components passing the BPF 40 have an identical wavelength characteristic shown in FIG. 8(*b*) and reach the CCD camera 10 similarly to the embodiment 2. And the CCD camera 10 takes in the light forming the images of the driver 1. On the other hand, the light forming the images of the driver 1 from the LED 20 which passes through the half mirror 30 and is reflected b the half mirror 31 (through the optical paths 13, 15) does not reach the CCD camera 13 because almost all the light components are intercepted by the BPF 43 having a wavelength characteristic shown in FIG. 27. Only the images of the driver 1 irradiated by the disturbance light of light components in the vicinity of 800 nm wavelength are input to the CCD 13. The image processing means 600 operates the differential images of the images obtained by the CCD camera 10 and the images obtained by the CCD camera 13 to obtain the images only by the infrared ray LED 20 illuminating light similarly to the embodiment 9. Since the influence of disturbance light is eliminated by the signal processing in these images, the brightness of pupils is greatly high in these images identically to those obtained by each of the aforementioned embodiments.

EMBODIMENT 17.

Figure 28:
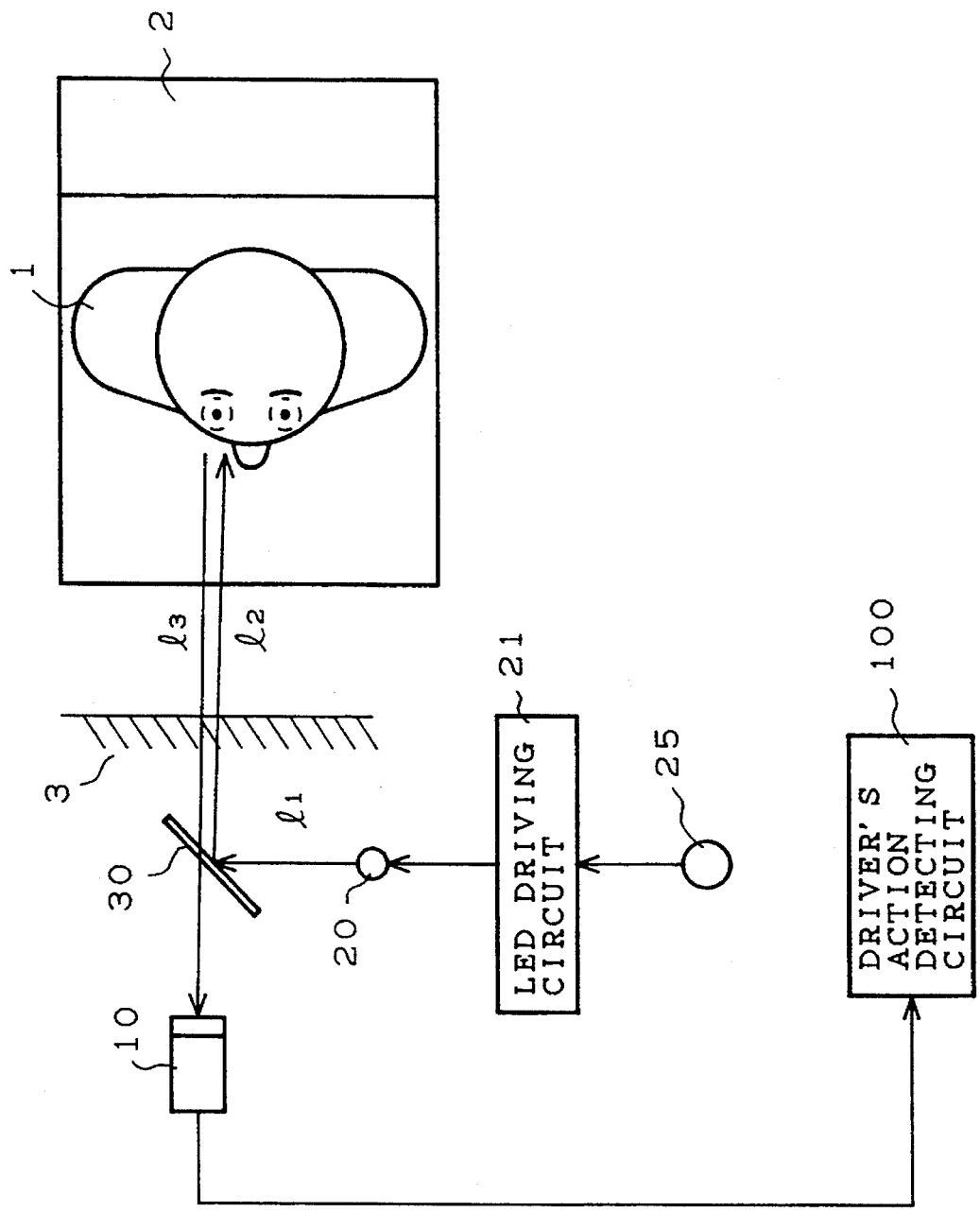
FIG. 28 is a block diagram showing the driver photographing apparatus of the embodiment 17 of the invention.

FIG. 28 is a block diagram showing the driver photographing apparatus of the embodiment 17 of the invention, which provided with an illuminance sensor 25 for measuring the illumingnee inside a car. An illuminating means composed of, for example, the LED 20 is constructed to be able to change its emission light intensity according to the illuminance inside the car detected by the illuminance sensor 25 in this embodiment. Because the driver photographing apparatus configured in such a manner can photograph a driver in a constant illuminance without being influenced by disturbance light, the contrast of the obtained face images becomes constant, and consequently, always distinct images reflected on retinas can be obtained.

EMBODIMENT 18.

Figure 29:
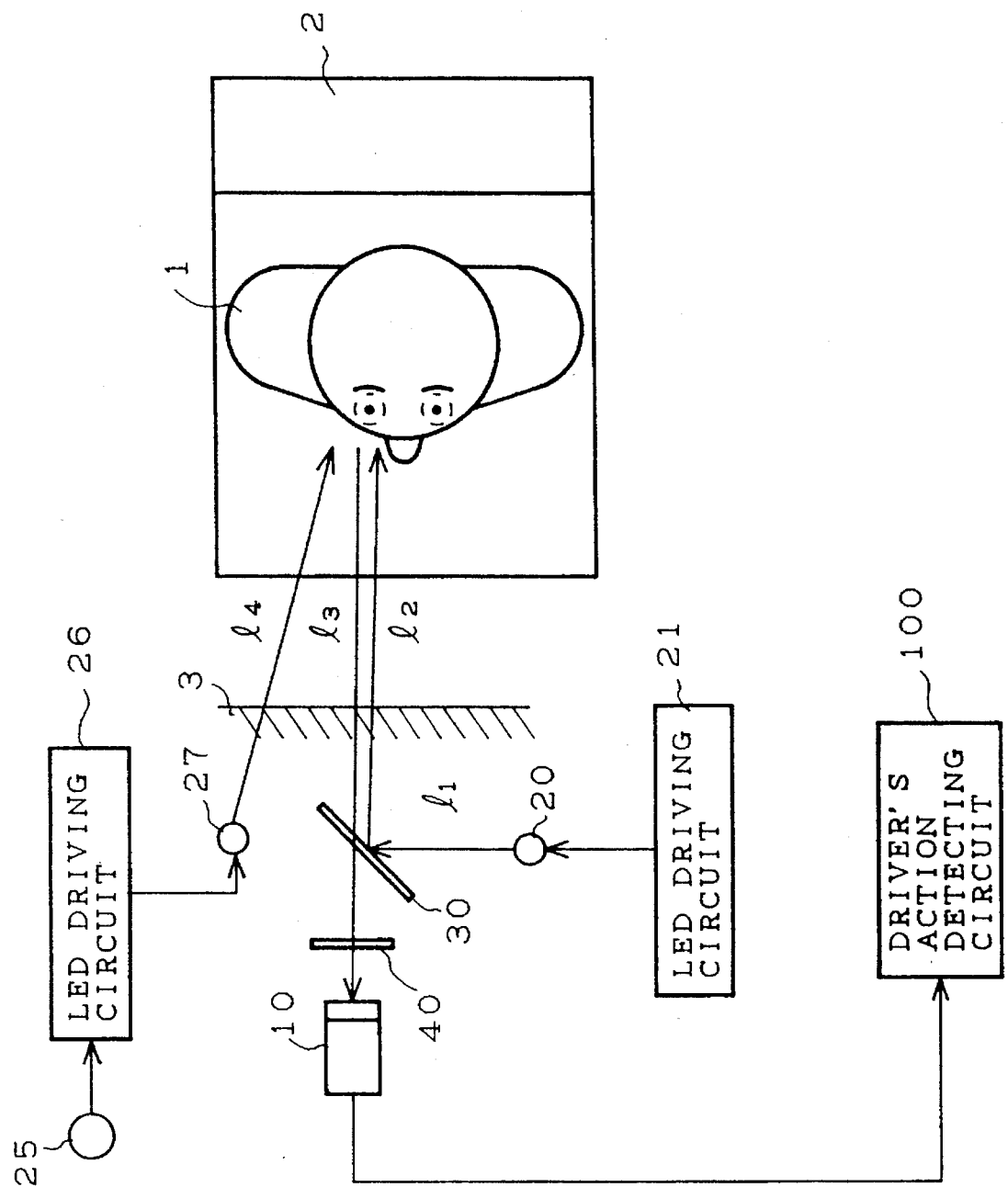
FIG. 29 is a block diagram showing the driver photographing apparatus of the embodiment 18 of the invention.

FIG. 29 is a block diagram showing the driver photographing apparatus of the embodiment 18 of the invention. This embodiment is provided with an illuminance sensor 25 for measuring the illuminance inside a car, and is composed to vary the emission light intensity of the second LED 27 illuminating the driver 1, the LED 27 being disposed at a different position from that of the LED 20, namely not at a coaxially irradiating position, in accordance with the illuminance in the car detected by the illuminance sensor 25 by means of the LED driving circuit 26. In the driver photographing apparatus configured in such a manner, the influence by disturbance light becomes constant, then the contrast of the obtained face images becomes constant, and consequently, always clear images reflected on retinas can be obtained.

Also, the aforementioned embodiments 17, 18 are provided with the illuminance sensors 25 measuring the illuminance inside a car, however it may be applicable to vary the illuminating light intensity so that the average value of the outputted signals from the CCD 10 falls in a prescribed range by measuring the outputted signals from the CCD 10 instead of providing the illuminance sensor 25.

Otherwise, it may be applicable to change the illuminating light intensity by means of the headlight turning signals without providing the illuminance sensor 25.

EMBODIMENT 19.

Figure 30:
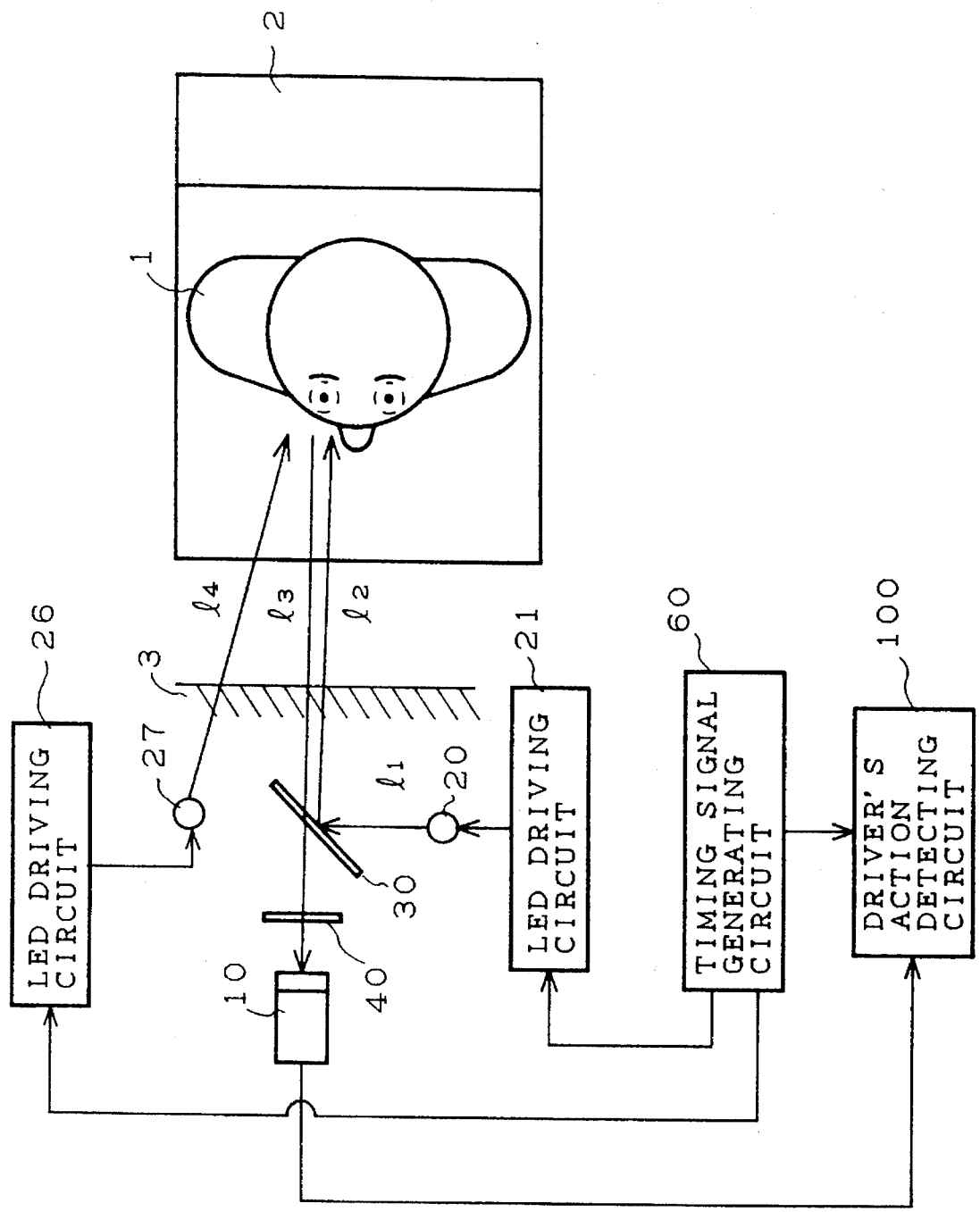
FIG. 30 is a block diagram showing the driver photographing apparatus of the embodiment 19 of the invention.

FIG. 30 is a block diagram showing the driver photographing apparatus of the embodiment 19 of the invention. The embodiment is provided with the second LED 27 disposed at a different position from that of the LED 20, i.e. not at the coaxially irradiating position, like the embodiment 18, in order that the illuminance by the emission light of the LED 27 on the face of the driver 1 becomes almost the same level as that by the emission light of the LED 20. Then, the driver 1 is illuminated by the LED 20 and the second LED 27 alternately by exchanging them in accordance with the timing signals from the timing signal generating circuit 60. And the driver's action detecting circuit 100 operates the differential images of each image obtained correspondingly to each LED's exchanging, then the images, where the brightness difference between the pupil parts and the other parts on the face is large, can be obtained. Thus, the influence of the illuminating of the face by the illuminating light can be removed, and obvious images reflected on retinas can be photographed. Furthermore, because the images obtained by the illumination of the second LED 27 has much information, other features of the driver 1 can be caught even in the nighttime by exchanging the illuminating light to the second LED 27 by means of the timing signals from the timing signal generating circuit 60.

EMBODIMENT 20.

Figure 31:
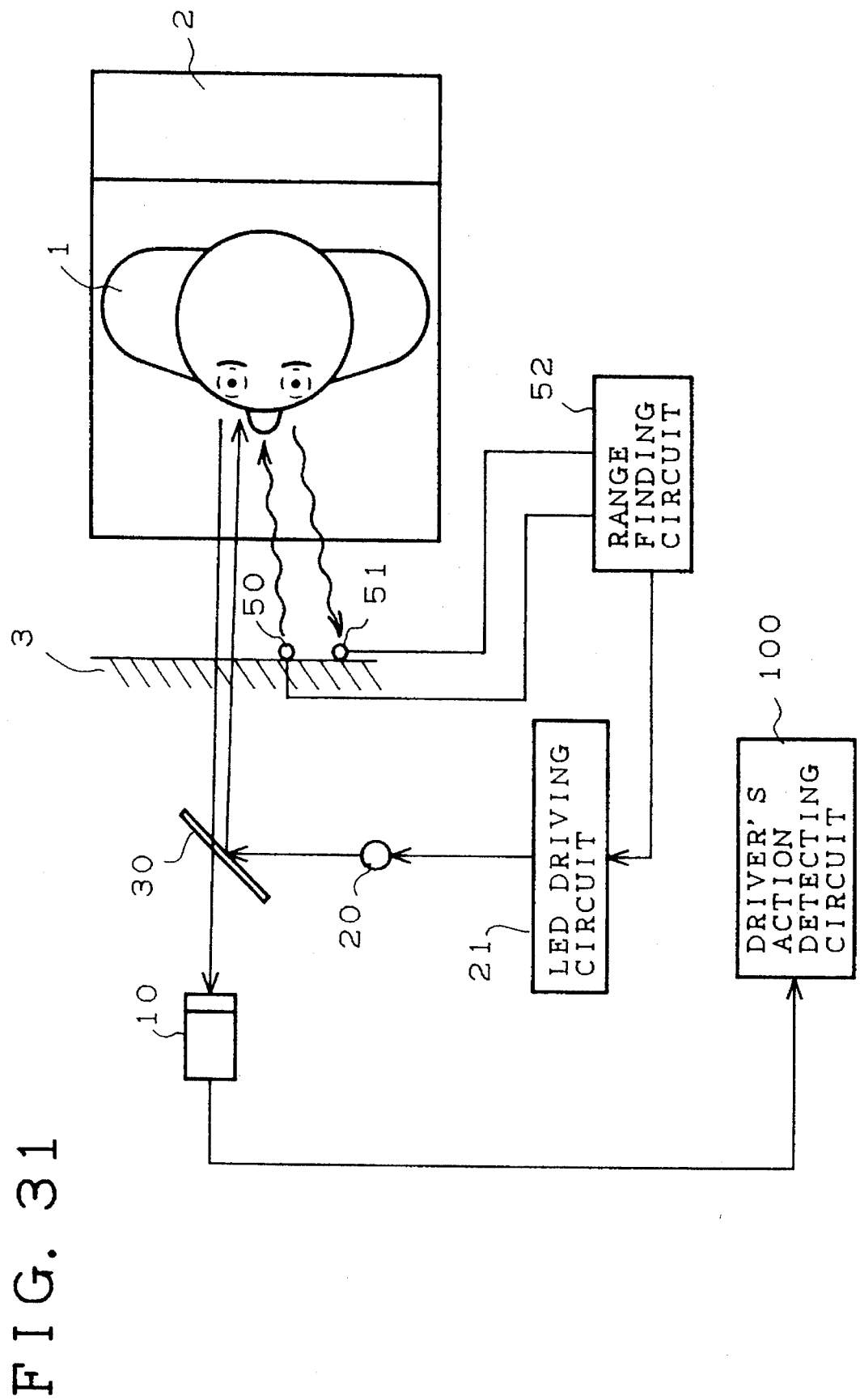
FIG. 31 is a block diagram showing the driver photographing apparatus of the embodiment 20 of the invention.

FIG. 31 is a block diagram showing the driver photographing apparatus of the embodiment 20 of the invention. In FIG. 31, reference numeral 50 designates an ultrasonic transmitter installed on the instrument panel 3; numeral 51 designates an ultrasonic receiver: and numeral 52 designates a range finding circuit.

Next, the operation of this embodiment will be described.

The ultrasonic transmitter 50 transmits pulses to the driver 1, and the ultrasonic receiver 51 receives the echoes of the transmitted ultrasonic waves. The range finding circuit 52 measures the distances from the positions of the transmitter 50 and the receiver 51 to the driver 1 by means of the time differences between the transmission time and the reception time of the ultrasonic waves. The LED driving circuit 21 receives the measured distances and varies the light intensity of the LED 20 in accordance with the measured distance so as to strengthen the illuminating light when the distance is large. As a result, the contrast of obtained face images becomes constant, thus clear images reflected on retinas can always be obtained.

EMBODIMENT 21.

Figure 32:
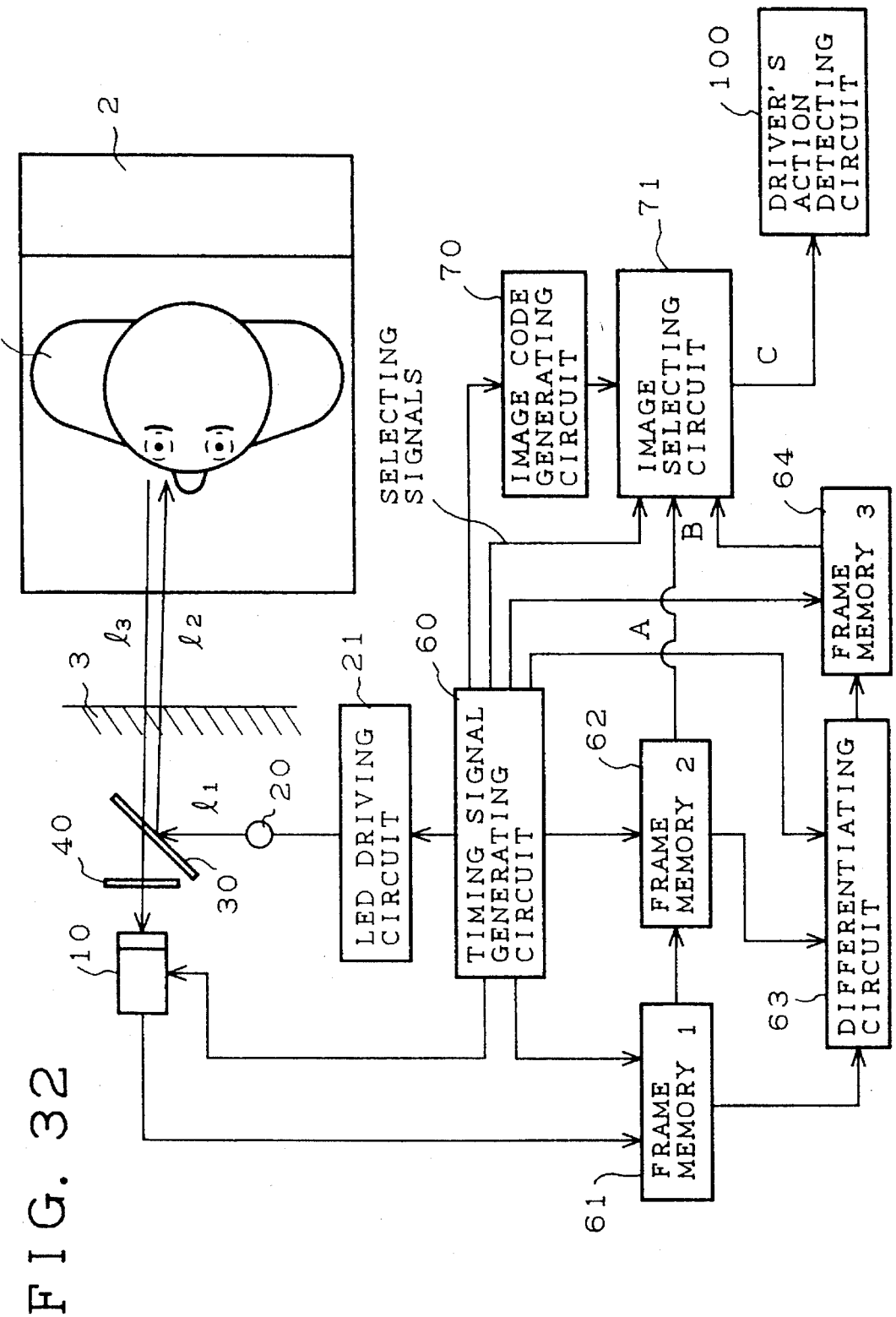
FIG. 32 is a block diagram showing the driver photographing apparatus of the embodiment 21 of the invention.

FIG. 32 is a block diagram of the driver photographing apparatus of the embodiment 21 of the invention. In FIG. 32, reference numeral 70 designates an image code generating circuit; and numeral 71 designates an image selecting circuit. Moreover, FIG. 33 is a timing chart for explaining the operation of the embodiment 21. In this embodiment 21, images are given discriminating signals, and the kinds of the images become capable of being discriminated by the driver's action detecting circuit 100.

Next, the operation of the embodiment 21 will be described.

In FIG. 32, the image code generating circuit 70 generates code signals (in the order of 1, 2, 3 . . . ) every frame according to the timing signals from the timing signal generating circuit 60. The image selecting circuit 71 regularly selects a content between the contents of the frame memory 2 (image signals A) and the contents of the frame memory 3 (image signals B) in accordance with the selecting signals from the timing signal generating circuit 60 as shown in FIG. 33, and the selecting circuit 71 superimposes code signals on the selected output signals C to transmit them to the driver's action detecting circuit 100.

Besides, the discriminating signals may be composed of the codes in the order of 1, 2, 1, 2 . . . instead of the codes in the order of 1, 2, 3, 4 . . . .

Also, the selection of images are not restricted to the exchange between the frame memory 2 and the frame memory 3. It may be applicable to select only the contents of frame memory 2 and to give codes to the contents of the memory 2 so as to be in the order 1, 2, 1, 2 . . . . In this case, the codes are defined in order that the code 1 means the LED's turning on and the code 2 means the LED's turning off.

Besides, the camera is not restricted to the CCD camera 10 in aforementioned embodiments. For example, a CID camera will do.

Also, the photographing system of the embodiment was explained about one camera, but plural sets of a coaxially irradiating illumination and a camera will do.

Furthermore, the coaxially irradiating illumination is explained only about a case using a half mirror, however the illumination method is not restricted to such the method, and any configuration of the coaxially irradiating illumination will do. For example, such configuration that a light emitting device is placed at the center of the optical path of camera lenses and the light emitted from the device illuminates the driver 1 will do.

It will be appreciated from the foregoing description that, according to the first aspect of the invention, an illuminating means and a light input means are arranged in order that the illuminating light irradiating direction of the illuminating means and an optical axis connecting the driver and the light input means take almost the same axis at least near the driver, and consequently, the invention has an effect capable of detecting the positions of eyes easily by means of a simple image processing techniques.

Furthermore, according to the second aspect of the invention, a disturbance light limiting means limiting the disturbance light is located on the optical path connecting a light input means with a driver, and consequently, clear images reflected on retinas can be obtained even if the disturbance light is strong.

Furthermore, according to the third aspect of the invention, a disturbance light limiting means is located on an optical path connecting an illuminating means and a driver and connecting a light input means and the driver, and consequently, the influence due to temperature changes can be decreased and the images formed by the disturbance light can be removed.

Furthermore, according to the fourth through sixth aspects of the invention, even if emission light wavelengths' shiftings of LEDs were to occur, a wavelength characteristics compensating means compensates the influence of the shiftings, and consequently, the apparatus of the invention can photograph obvious images reflected on retinas.

Furthermore, according to the seventh aspect of the invention, the driver photographing apparatus obtains the image signals of a driver both in the case where illuminating light exists or not, and the apparatus obtains images reflected on retinas from the difference image signals of both of the aforementioned image signals. Consequently, the influence of disturbance light is eliminated by the signal processings, and the obvious images reflected on the retinas can be photographed.

Furthermore, according to the eighth aspect of the invention, the driver photographing apparatus is constructed to input the images of a driver to the apparatus for a prescribed time period corresponding to the existence of illustrating light, and consequently, blurrings become smaller. Thus, obvious images can be photographed even if the movement of eyes is fast.

Furthermore, according to the ninth aspect of the invention, the images of a driver ace input for a prescribed time over the time of illuminating light's existing and the time of the illuminating light's nonexisting, and consequently, obtained differential images have a difference corresponding to the existence of the illuminating light, thus obvious images can be photographed even if the movement of the driver is fast.

Furthermore, according to the tenth aspect of the invention, the driver photographing apparatus is provided with a first disturbance light limiting means passing through the light components of an illuminating means and the first light input means to which driver images formed by the light components mentioned above are input, a second disturbance light limiting means passing through the different light components from the light components mentioned above and a second light input means to which driver images formed by the different light components are input, and an image processing means outputting each image obtained by each light input means or images produced by taking the difference of each aforementioned images, and consequently, the influence of the disturbance light is removed, obvious images reflected on retinas can be photographed.

Furthermore, according to the eleventh and twelfth aspects the invention, the driver photographing apparatus is constructed to change the illuminating light intensity of an irradiating means or the illuminating light intensity of a second illuminating means disposed at a different position from that of the aforementioned illuminating means according to the luminous intensity inside a car, and consequently, the contrast of obtained face images becomes constant, and clear images reflected on retinas can be always obtained.

Furthermore, according to the thirteenth aspect of the invention, the driver photographing apparatus comprises a first illuminating means disposed in such a way that the illuminating light irradiating direction and the light axis of a light input means take almost the same axis near a driver, a second illuminating means disposed at a different position from the first illuminating means and illuminating the driver, and an exchanging means exchanging the first illuminating means and the second illuminating means to illuminate the driver, and consequently, obvious images reflected on retinas can be photographed by operating the differential images of each image obtained in accordance with exchanges of each illuminating means. Moreover, because the images obtained by the second illuminating means have much information, other features of the driver can be caught even in the nighttime by exchanging the illumination to the second illuminating means by means of the exchanging means.

Furthermore, according to the fourteenth aspect of the invention, illuminating light intensity is varied in proportion to the distance between a driver and an illuminating means, and consequently, the driver is always illuminated by constant illuminance, and the contrast of obtained face images becomes constant, such that clear images reflected on retinas can be obtained.

While preferred embodiments of the invention have been described by means of specific terms, such description is for illustrative purposes only, and it is to be understood that changes and variations may be made without departing from the spirit or scope of the following claims.

What is claimed is:

1. A driver photographing apparatus for monitoring a driver in a vehicle wherein background light is present, the driver having eyes with pupils, the photographing apparatus comprising:

an illuminating means for illuminating the driver with a first beam of light along a first optical path, the first beam of light being reflected from the driver to form a second beam of light along a second optical path, the second beam of light having a frequency;

a photographing means for forming an image based upon light received at the photographing means, the photographing means being disposed along the second optical path so that the photographing means receives the second beam of light and forms an image of said driver, the first and second optical paths being along a substantially same axis; and limiting means for limiting an effect of the background light on the image, the limiting means including means for limiting the effect on the image of components of the background light at the frequency of the second beam of light.

2. The driver photographing apparatus according to claim 1, wherein the limiting means includes passing means for passing the second beam of light and for limiting passage of the background light through the passing means, said passing means being disposed on the second optical path between the driver and the photographing means.

3. The driver photographing apparatus according to claim 1, wherein the limiting means further includes:

an illuminating light controlling means for turning said illuminating means on and off; and an image processing means, coupled to the photographing means, for outputting one of a first image of said driver formed when the illuminating means is turned on, a second image of said driver formed when the illuminating means is turned off, and a third image of said driver that is formed from a difference between the first image and the second image.

4. A driver photographing apparatus for monitoring a driver in a vehicle wherein disturbance light is present, the driver having eyes with pupils, the photographing apparatus comprising:

an illuminating means for illuminating the driver with a first beam of light along a first optical path, the first beam of light being reflected from the driver to form a second beam of light along a second optical path, the second beam of light having a frequency, the first and second optical paths being along a substantially same axis; and a photographing means for forming an image based upon light received at the photographing means, the photographing means being disposed along the second optical path so that the photographing means receives the second beam of light and forms an image of said driver;

limiting means for limiting an effect of the background light on the image, the limiting means including means for limiting the effect on the image of components of the background light at the frequency of the second beam of light, wherein the limiting means further includes;

an illuminating light controlling means for turning said illuminating means on and off; and an image processing means, coupled to the photographing means, for outputting one of a first image of said driver formed when the illuminating means is turned on, a second image of said driver formed when the illuminating means is turned off, and a third image of said driver that is formed from a difference between the first image and the second image; and wherein said photographing apparatus includes a light input controlling means for controlling time periods during which light is received at the photographing means to correspond to time periods when the illuminating means is turned on.

5. The driver photographing apparatus according to claim 4, wherein said light input controlling means further controls the time periods during which light is received at the photographing means to correspond to time periods when the illuminating means is turned off.

6. A driver photographing apparatus to detect an action of a driver in a vehicle, the driver having pupils, the driver photographing apparatus comprising:

a light source that generates a first beam of light along a first path, the first beam of light having an intensity;

a deflector that deflects the first beam of light to create a second beam of light along a second path, the second path extending along an axis between the deflector and the driver, the second beam of light being reflected from the driver to form a third beam of light along a third path that extends along the axis;

a sensor that senses the third beam of light to form an image of the driver, the sensor being positioned along the axis; and a detecting circuit, coupled to the sensor, that detects a position of the driver's pupils from the image to determine the action of the driver.

7. A driver photographing apparatus to detect an action of a driver in a vehicle wherein background light is present, the driver having pupils, the driver photographing apparatus comprising:

a light source that generates a first beam of light along a first path, the first beam of light having an intensity;

a deflector that deflects the first beam of light to create a second beam of light along a second path, the second path extending along an axis between the deflector and the driver, the second beam of light being reflected from the driver to form a third beam of light along a third path that extends a sensor that senses the third beam of light to form an image of the driver, the sensor being positioned along the axis;

a first frame memory, coupled to the sensor, that stores a first image formed solely by the background light;

a second frame memory, coupled to the sensor, that stores a second image formed at the sensor by the third beam of light and the background light;

a timing circuit that prevents the first beam of light from reaching the driver for a first predetermined amount of time while the first image is formed, and that enables the first beam of light to reach the driver for a second predetermined amount of time while the second image is formed;

a subtracting circuit that subtracts the first image stored in the first frame memory from the second image stored in the second frame memory to form an enhanced image; and a detecting circuit, coupled to the sensor, that detects the action of the driver from the enhanced image.

8. The driver photographing apparatus according to claim 6, wherein background light having an intensity is present in the vehicle, and wherein the apparatus further comprises:

a filter positioned to substantially prevent the background light from reaching the sensor.

9. A driver photographing apparatus to detect an action of a driver in a vehicle, the driver having eyes with pupils, the driver photographing apparatus comprising:

an image sensor positioned opposite the driver along an axis;

a light source that directs an illuminating light beam toward the driver along the axis to form a reflected light beam that travels along the axis to the sensor, the reflected beam forming an image of the driver at the image sensor; and detecting means, coupled to the image sensor, for detecting a position of the driver's pupils from the image to determine the action of the driver.

10. The driver photographing apparatus according to claim 9, wherein the vehicle has background light that can have an effect on the image, and wherein the apparatus further comprises:

means for substantially eliminating the effect of the background light on the image of the driver.

11. A driver photographing apparatus for detecting an action of a driver in a vehicle in which background light is present, the apparatus comprising:

a light source that generates a first beam of light along a first path, the first beam of light having a frequency;

a deflector that deflects the first beam of light to create a second beam of light along a second path, the second path extending along an axis between the deflector and the driver, the second beam of light being reflected from the driver to form a third beam of light along a third path that extends along the axis;

a sensor that senses light received at the sensor and forms an image based upon the light received at the sensor, the sensor being positioned along the axis in the path of the third beam of light;

limiting means for limiting an effect of the background light on the image, the light limiting means including means for limiting the effect on the image of components of the background light at the frequency of the first beam of light; and a detecting circuit, coupled to the sensor, that determines the action of the driver based on the image.

12. The driver photographing apparatus according to claim 11, wherein the detecting circuit determines the action of the driver based on an enhanced image, and wherein the limiting means further includes:

means, coupled to the sensor, for storing a first image formed from the third beam of light and the background light received at the sensor;

means, coupled to the sensor, for storing a second image formed solely by the background light received at the sensor;

a timing circuit that prevents the first beam of light from reaching the driver for a first predetermined amount of time while the second image is formed, and that enables the first beam of light to reach the driver for a second predetermined amount of time while the first image is formed; and a subtracting circuit that subtracts the second image from the first image to form the enhanced image.

13. A driver photographing apparatus to detect an action of a driver in a vehicle in which background light is present, the apparatus comprising:

an image sensor positioned opposite the driver along an axis;

a light source that directs an illuminating light beam toward the driver along the axis to form a reflected light beam that travels along the axis to the sensor, the reflected beam forming an image of the driver at the image sensor, the reflected light beam having a frequency;

a limiting means for limiting an effect of the background light on the image, the limiting means including means for limiting the effect on the image of components of the background light at the frequency of the reflected light beam; and a detecting circuit, coupled to the image sensor, that determines the action of the driver based on the image.

* * * * *